United States Patent
Tropsch et al.

(10) Patent No.: US 7,074,749 B2
(45) Date of Patent: Jul. 11, 2006

(54) OXOALCOHOL-BASED DETERGENT

(75) Inventors: Juergen Tropsch, Roemerberg (DE); Heiko Maas, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 259 days.

(21) Appl. No.: 10/311,210

(22) PCT Filed: Jun. 13, 2001

(86) PCT No.: PCT/EP01/06709

§ 371 (c)(1),
(2), (4) Date: Dec. 16, 2002

(87) PCT Pub. No.: WO01/96508

PCT Pub. Date: Dec. 20, 2001

(65) Prior Publication Data

US 2004/0009889 A1    Jan. 15, 2004

(30) Foreign Application Priority Data

Jun. 16, 2000 (DE) ................................. 100 29 692
Jun. 16, 2000 (DE) ................................. 100 29 693

(51) Int. Cl.
  *C11D 1/722* (2006.01)
  *C11D 3/20* (2006.01)
  *C11D 3/37* (2006.01)
  *C11D 11/04* (2006.01)

(52) U.S. Cl. ....................... 510/356; 510/360; 510/413; 510/421; 510/475; 8/137; 134/25.2; 134/25.3; 134/39; 134/42

(58) Field of Classification Search ................ 510/356, 510/360, 413, 421, 475; 8/137; 134/25.2, 134/25.3, 39, 42
See application file for complete search history.

(56) References Cited

U.S. PATENT DOCUMENTS

| 3,420,875 A | 1/1969 | Di Salvo et al. |
| 3,462,525 A | 8/1969 | Levinsky et al. |
| 3,524,864 A | 8/1970 | Rubinfeld et al. |
| 3,887,806 A | 6/1975 | Rodak et al. |
| 5,227,446 A | 7/1993 | Denzinger et al. |

(Continued)

FOREIGN PATENT DOCUMENTS

DE         41 06 355         9/1992

(Continued)

OTHER PUBLICATIONS

Ullmann's Encyclopedia of Industrial Chemistry, vol. A8, No. 5, pp. 315-448 1986.

(Continued)

*Primary Examiner*—Brian P. Mruk
(74) *Attorney, Agent, or Firm*—Oblon, Spivak, McClelland, Maier & Neustadt, P.C.

(57) ABSTRACT

The invention describes detergents and cleaners comprising an effective proportion of one or more surfactants of the formula I

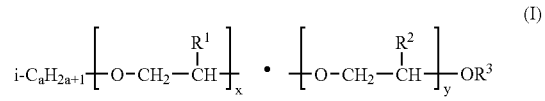

in which
a is one of the numbers 11, 12, or 13,
$R^1$ and $R^2$ are different and are each hydrogen or alkyl radicals $R^3$ is hydrogen, or a sulfato or phosphate radical,
x and y are each a number from 0 to 200,
and further known auxiliaries and additives customary in detergents and cleaners and optionally in addition further surfactants.

11 Claims, 3 Drawing Sheets

U.S. PATENT DOCUMENTS

| | | | |
|---|---|---|---|
| 5,360,569 | A | 11/1994 | Madison et al. |
| 5,399,286 | A | 3/1995 | Funhoff et al. |
| 5,756,456 | A | 5/1998 | Ho et al. |
| 6,057,284 | A * | 5/2000 | Baur et al. .................. 510/506 |
| 6,222,077 | B1 * | 4/2001 | Singleton .................... 568/909 |
| 2004/0186325 | A1 | 9/2004 | Maas et al. |

FOREIGN PATENT DOCUMENTS

| | | |
|---|---|---|
| DE | 43 13 909 | 11/1994 |
| DE | 43 39 713 | 5/1995 |
| DE | 44 15 623 | 11/1995 |
| EP | 0 001 004 | 3/1979 |
| EP | 0 396 303 | 11/1990 |
| EP | 0 451 508 | 10/1991 |
| EP | 0 453 003 | 10/1991 |
| EP | 0 454 126 | 10/1991 |
| EP | 0 511 037 | 10/1992 |
| EP | 0 581 452 | 2/1994 |
| EP | WO 97/46311 | * 12/1997 |
| WO | 94/01486 | 1/1994 |
| WO | 94/04585 | 3/1994 |
| WO | 94/21777 | 9/1994 |
| WO | 95/11225 | 4/1995 |
| WO | 97/19159 | 5/1997 |
| WO | WO 97/38957 | 10/1997 |
| WO | WO 99/19440 | 4/1999 |
| WO | WO 00/39058 | 7/2000 |

OTHER PUBLICATIONS

Ullmann's Encyclopedia of Industrial Chemistry, vol. A7, pp. 137-151 1986.

Ullmann's Encyclopedia of Industrial Chemistry, vol. A18, pp. 235-236.

K.J. Ivin: "Olefin Metathesis" Academic Press, London, Houben-Weyl, E18, pp. 1163-1223 1983, Not Translated.

Robert L. Banks: "Discovery and development of olefin disproportionation" CHEMTECH, pp. 112-117 1986.

Matthias Beller et al.: "Progress in hydroformylation and carbonylation" Journal of Molecular Catalysts, vol. A104, pp. 17-85 1993.

Ullmann'Encyclopedia of Industrial Chemistry, vol. A5, pp. 217-234.

G. Gee et al.: "The polymerisation of epoxides. Part III. The polymerization of propylene oxide by sodium alkoxides" Journal of The Chemical Society, pp. 4298-4303 1961.

Von Bernhard Wojtech: "Zur darstellung hochmolekularer polyaethylenoxyde" Makromol. Chem., vol. 66, pp. 180-195 1963, Not Translated.

A.M. Eastham: "Chapter 10: Epoxides" The Chemistry of Cationic Polymerization, P.H. Plesch, Ed., Pergamon Press, New York, pp. 403-430 1963.

Ullmann's Encyclopedia of Industrial Chemistry, vol. A25, pp. 779-783 1994.

Fausto Ramirez et al.: "Synthesis of phosphodiesters: The cyclic enediol phosphoryl (CEP) method" SYNTHESIS, pp. 449 1985.

Fausto Ramirez et al.: "Synthesis of phosphodiesters: The cyclic enediol phosphoryl (CEP) method" SYNTHESIS, pp. 449-488 1985.

* cited by examiner

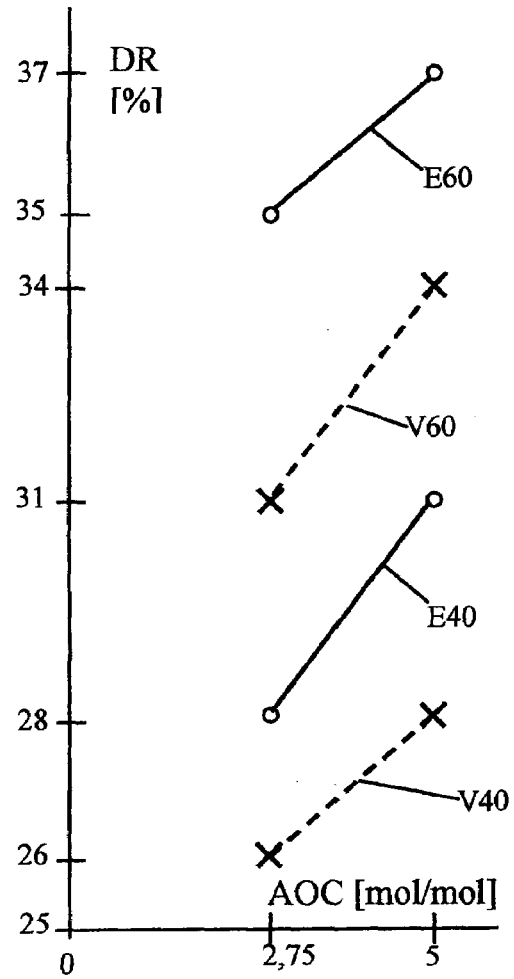
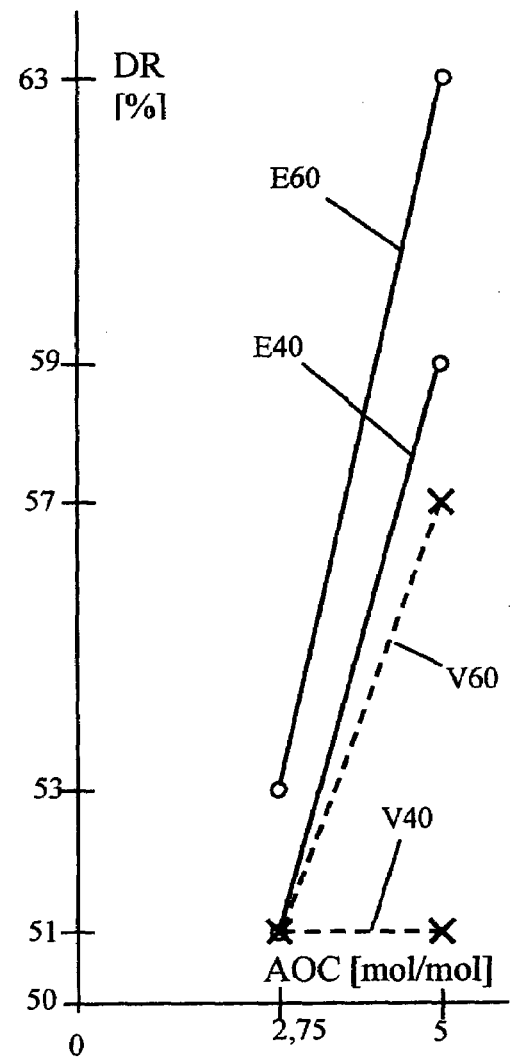
EMPA 101
Fig. 2a
wfk 10 D
Fig. 2b

OXOALCOHOL-BASED DETERGENT

The present invention relates to detergents and cleaners which have an effective proportion of nonionic surfactants or anionic surfactants based on oxo alcohols having 11 to 13 carbon atoms which, as a result of their structure, are markedly superior to the closest comparable known surfactants. The invention also relates to a process for the preparation of detergents and cleaners using said surfactants, and to the use of the detergents and cleaners according to the invention.

For the purposes of this invention, detergents generally serve for the washing of more or less flexible materials, preferably those which comprise natural, synthetic or semi-synthetic fiber materials, or consist thereof and which, accordingly, at least partially have a textile character.

Detergents of this type have been frequently described in the prior art. A very good overview of the mode of action and the composition of detergents is given, for example, in Ullmann's Encyclopedia of Industrial Chemistry, 5$^{th}$ edition, Vol. A8, (1986), pages 315 ff, keyword "Detergents".

For the purposes of this invention, cleaners are generally used for the cleaning of surfaces which have no or only a few small pores and consequently have no or only low absorption capacity.

Cleaners of this type have been frequently described in the prior art. A very good overview of the mode of action and the composition of cleaners is given, for example, in Ullmann's Encyclopedia of Industrial Chemistry, 5$^{th}$ edition, Vol. A7, (1986), pages 137 ff.

The detergents and cleaners comprise one surfactant or two or more surfactants from identical or different surfactant groups and usually further auxiliaries and additives which are either required for the formulation and/or which serve to adapt the detergents and cleaners to the intended specific use or the type of application (washing or cleaning by hand or in machines). Constituents which can be used alongside the various surfactants in varying combinations and proportions in many detergents and cleaners are, for example, builders (sequestering agents) and cobuilders, pH regulators, such as inorganic or organic acids, inorganic or organic bases and buffer systems, dispersants, soil-suspending agents, thickeners, enzymes, bleaching systems, hydrotropic compounds as solubility promoters or solubilizers, such as urea or alcohols, foam regulators for stabilizing or suppressing foam, skin protectants and corrosion inhibitors, disinfecting compounds or systems, for example those which comprise iodine or which liberate chlorine or hypochlorous acid, such as dichloroisocyanurate, perfume, dyes, and biocides.

Detergents often contain alongside with the ingredients listed above optical (fluorescent) brighteners, antiredeposition agents, extenders and formulating agents, cleaners may contain in addition to the above constituents organic solvents, finely divided abrasive components, such as quartz or marble powder, chalk, diatomaceous earth, pumice, polishing rouge or emery.

A significant proportion of the cleaning action of the detergents and cleaners described in the prior art is attributed to the surfactants present therein. The surfactants used are ionic surfactants and, more specifically, anionic surfactants, such as alcohol sulfates, alcohol ether sulfates, alkylbenzenesulfonates, α-olefinsulfonates, sulfosuccinates, and also cationic surfactants, such as $C_8$ to $C_{16}$-dialkyldimethylammonium halides, dialkoxy-dimethylammonium halides or imidazolinium salts with a long-chain alkyl radical.

The use of amphoteric surfactants, for example derivatives of secondary or tertiary amines, such as $C_6$–$C_{18}$-alkylbetaines or $C_6$–$C_{15}$-alkylsulfobetaines or amine oxides, such as alkyldimethylamine oxides, has also already been described.

Nonionic surfactants, including, in particular, alkoxylates and polyglycosides of longer-chain and long-chain alkanols having, in particular, 8 to 20 carbon atoms, and alkoxylates of alkylamines and alkylamides are also used in detergents and cleaners. In particular, it is also known to use oxo alcohols having 10 to 13 carbon atoms in the form of their phosphoric or sulfuric esters, and alkoxylates of these oxo alcohols directly or in the form of their phosphoric or sulfuric esters as surfactants in detergents and cleaners.

In the interest of the most economical material use possible, high efficiency and, last but not least, low environmental pollution, the manufacturers of detergents and cleaners strive to continually improve the effectiveness of their products and in particular of the surfactants present therein.

Surprisingly, we have now found that the detergents and cleaners according to the invention described below display an effectiveness which is considerably superior to the closest comparable known compositions.

The present invention accordingly provides detergents and cleaners comprising an effective proportion of one or more surfactants of the formula I

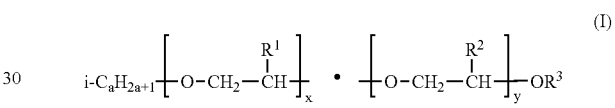

in which
a is one of the numbers 11, 12, or 13,
$R^1$ and $R^2$ are different and are each hydrogen or alkyl radicals of the formula $C_nH_{2n+1}$—,
$R^3$ is hydrogen, or a sulfato or phosphate radical,
n is a number from 1 to 16, x is a number from 0 to 200, and y is a number from 0 to 200,
and further known auxiliaries and additives customary in detergents and cleaners and optionally in addition further surfactants.

In the following description reference is made to drawings FIGS. 1 to 3.

FIG. 1 gives a view on the way of synthesis, leading to the detergents and cleaners of this invention.

FIGS. 2a and 2b illustrate the washing capability of the detergents of this invention and of detergents which are comparable with respect to their structure, but are outside the scope of this invention. In both cases the washing tests were performed using detergents with varied contents of alkylenoxid groups and using two different soiled fabrics. The increase of the light remittance of the washed fabrics is used as a measure for the cleaning activity of the detergents used.

FIG. 3 illustrates the cleaning capability of the cleaners of this invention (curve 1) and of cleaners which are comparable with respect to their structure, but are outside the scope of this invention (curve 2). In both cases the cleaning tests were performed using detergents with varied contents of alkylenoxid groups. The removal of oil from the surface of a metallic plate, expressed in % of the amount originally applicated to the plate, is used as a measure for the cleaning activity of the cleaners used.

The abbreviations used in FIGS. 2a, 2b and 3 have the meanings listed below:

| | |
|---|---|
| AOC: | Content of alkyleneoxide units in the detergent or cleaner, respectively. |
| DR: | Degree of light remittance, % of the irradiated amount of light. |
| EMPA 101 and wfk 10 D: | Designations for soiled test fabrics. |
| E40 and E60: | Curves for wash at 40° C. or 60° C., respectively, using detergent according to the invention. |
| V40 and V60: | Curves for wash at 40° C. or 60° C., respectively, using comparative detergent. |
| OR: | Oil removal, given in % of the originally amount. |

It is of considerable importance for the high effectiveness of the detergents and cleaners according to the invention that the i-$C_aH_{2a+1}$ radical present in the surfactants of the formula I is derived from an oxo alcohol obtained by hydroformylation of a decene, dodecene or a mixture of these olefins which, in turn, has been prepared by dimerizing n-pent-2-ene, hex-3-ene or mixtures of these compounds.

The minimum proportion of the surfactants of the formula I based on the total weight of the detergents and cleaners according to the invention is such that the action of this additive is significant.

The proportion of the surfactants to be used according to the invention is expediently set such that, in conjunction with the other constituents of the detergents and cleaners, an optimum cleaning action arises.

Good detergency, in particular very good primary detergency, of the detergents according to the invention is generally achieved if the proportion of the surfactants of the formula I in the detergent according to the invention, based on the total weight of the composition, is 0.01 to 50% by weight, preferably 0.1 to 40% by weight, in particular 0.5 to 30% by weight.

A good cleaning action of the cleaners according to the invention is generally achieved if the proportion of the surfactants of the formula I in the cleaners according to the invention, based on the total weight of the composition, is 0.01 to 40% by weight, preferably 0.1 to 30% by weight, in particular 0.1 to 20% by weight.

Preference is given to surfactants of the formula I in which a is 13.

Also advantageous are surfactants of the formula I in which n is a number from 1 to 8, preferably from 1 to 4, in particular 1 or 2.

In a further preferred group of surfactants of the formula I, $R^1$ and $R^2$ are different and are each hydrogen, methyl, ethyl or propyl.

Preference is also given to surfactants of the formula I in which x is a number from 1 to 50, in particular from 1 to 20, and y is a number from 0 to 50, in particular from 0 to 20.

Preference is also given to surfactants of the formula I in which the sum x+y is in the range from 1 to 200, preferably from 1 to 100, in particular from 1 to 50.

In a further specific embodiment, the detergents and cleaners according to the invention comprise at least an effective proportion of compounds of the formula I, but with the proviso that either the sum x+y is at least 1, or $R^3$ is not hydrogen.

The x ether chain members of the formula —$CH_2$—$CHR^1$— and the y ether chain members of the formula —$CH_2$—$CHR^2$— can be arranged in the ether chain in the compounds of the formula I in blocks or randomly.

The compounds of the formula I may be uniform substances, but they may also be mixtures in which various substances covered by formula I are mixed together. The components of these mixtures can differ with regard to the meanings of $R^1$, $R^2$ and also $R^3$, and with regard to the values of a, and in particular of x and y. The consequence of this is that the analytical values obtained during the elemental analysis of the surfactants of the formula I, for example the C and H values obtained for the oxo alcohol building group, and in particular the values of the alkoxy group determination, lead to fractional values for a, n, x and y when back-calculating to the structural formula. Of course, such substance mixtures are also surfactants according to the invention covered by the formula I which have the described advantages over the prior art.

For the purposes of this invention, detergents generally serve for the washing of more or less flexible materials, preferably those which comprise natural, synthetic or semi-synthetic fiber materials, or consist thereof and which, accordingly, at least partially have a textile character. The fiber-containing materials or materials consisting of fibers may in principle be in any form found in use or the preparation and processing. For example, fibers may be unarranged in the form of flocks or heaps, arranged in the form of threads, yarns, twists, or in the form of sheet structures, such as nonwovens, loden substances or felt, wovens, knits in all conceivable kinds of weave.

They may be crude fibers or fibers in any processing stages, and may be natural protein or cellulose fibers, such as wool, silk, cotton, sisal, hemp, coconut fibers or synthetic fibers, such as, for example, polyester, polyamide or polyacrylonitrile fibers.

The detergents according to the invention can also be used with particular advantage during the course of the processing of fiber materials, e.g. for the scouring of raw wool or for desizing fiber materials of all types.

The detergents according to the invention can also be used for the cleaning of fiber-containing materials, such as, for example, backed carpets with cut or uncut pile.

The cleaners according to the invention are particularly suitable for the cleaning of materials with a continuous, in particular hard, surface, i.e. of surfaces which have no or very few small pores and consequently have no or only low absorption capacity. Materials with continuous surfaces are predominantly hard, but can also be soft in the sense that they have a certain reversible or irreversible formability. Examples of materials with hard surfaces for whose cleaning the cleaners according to the invention are preferably used are metal, glass, enamel, ceramic. Typical objects made of these materials are, for example, metal toilet pans, cutlery, glass and porcelain crockery, bath tubs, wash basins, tiles, slabs and cured synthetic resins, such as decorative melamine resin surfaces on kitchen furniture or painted metal surfaces such as refrigerators and car bodies. The cleaners according to the invention are also very valuable auxiliaries in the preparation of printed circuits, for removing traces of grease and other impurities from copper- or silver-coated substrates prior to engraving and/or prior to assembly, and/or for completely removing soldering pastes or other flux residues after assembly.

The cleaners according to the invention can also be useful during the production of microchips. Materials with continuous, in particular hard, surfaces for the purposes of this invention can also have fissured surfaces, as are to be found, for example, in the case of metal-ceramic materials.

Examples of softer materials which can be cleaned with the cleaners according to the invention are, for example, sealed or painted woods, e.g. parquet or wall paneling, window frames, doors, plastic coverings such as floor coverings made of PVC or hard rubber, or rigid or flexible foams having largely continuous surfaces.

In particular, the cleaners according to the invention can, for example, be used as hand dishwashing detergents, machine dishwashing detergents, metal degreasers, glass cleaners, floor cleaners, all-purpose cleaners, high-pressure cleaners, neutral cleaners, alkaline cleaners, acidic cleaners, spray degreasers, dairy cleaners, large-kitchen cleaners, apparatus cleaners in industry, in particular in the chemical industry, as cleaners for car washes, but also as household all-purpose cleaners.

The compositions of the detergents and cleaners are of course adapted to the various purposes, as is known to the person skilled in the art from the prior art. For this purpose, all auxiliaries and additives appropriate for the purpose and known from the above-mentioned prior art can be added to the detergents and cleaners according to the invention.

In many cases, it is expedient to combine the surfactants of the formula I used according to the invention with other nonionic surfactants, such as alcohol alkoxylates, alkylamine alkoxylates, alkylamide alkoxylates, alkyl polyglucosides, or with ionic, preferably anionic, surfactants, such as longer-chain or long-chain alcohol sulfate/ether sulfates, alkylbenzenesulfonates, α-olefinsulfonates, sulfosuccinates, or with amphoteric surfactants, such as alkylamine oxides, or betaines.

Examples of surfactants of varying nature which are suitable for combination are given below:

Examples of suitable nonionic surfactants are alkoxylated $C_8$–$C_{22}$-alcohols, such as fatty alcohol alkoxylates or oxo alcohol alkoxylates. The alkoxylation can be carried out with ethylene oxide, propylene oxide and/or butylene oxide. Surfactants which can be used here are all alkoxylated alcohols which preferably contain two added molecules of an above-mentioned alkylene oxide. Also suitable here are block polymers of ethylene oxide, propylene oxide and/or butylene oxide, or addition products which contain said alkylene oxides in random distribution. 2 to 50 mol, preferably 3 to 20 mol, of at least one alkylene oxide is used per mole of alcohol. The alkylene oxide used is preferably ethylene oxide. The alcohols preferably have 10 to 18 carbon atoms. Alkoxylates with a broad or narrow alkylene oxide homolog distribution can be obtained depending on the type of alkoxylation catalyst.

A further class of suitable nonionic surfactants are alkylphenol alkoxylates, such as alkylphenol ethoxylates having $C_6$ to $C_{14}$-alkyl chains and 5 to 30 mol of alkylene oxide units.

Another class of nonionic surfactants are alkyl polyglucosides having 6 to 22, preferably 8 to 18, carbon atoms in the alkyl chain. These compounds mostly contain 1 to 20, preferably 1.1 to 5, glucoside units.

Another class of nonionic surfactants are N-alkylglucamides of the general structures

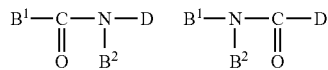

where $B^1$ is a $C_6$–$C_{22}$-alkyl, $B^2$ is hydrogen or $C_1$- to $C_4$-alkyl and D is a polyhydroxyalkyl radical having 5 to 12 carbon atoms and at least 3 hydroxyl groups. Preferably, $B^1$ is $C_{10}$–$C_{18}$-alkyl, $B^2$ is $CH_3$ and D is a $C_5$ or $C_6$ radical. Such compounds are obtained, for example, by the acylation of reductively aminated sugars with acid chlorides of $C_{10}$- to $C_{18}$-carboxylic acids.

Further suitable nonionic surfactants are the terminally capped fatty acid amide alkoxylates known from WO-A 95/11225 and of the formula

in which
$R^1$ is a $C_5$- to $C_{21}$-alkyl or alkenyl radical,
$R^2$ is a $C_1$- to $C_4$-alkyl group,
$A^1$ is a $C_2$- to $C_4$-alkylene,
y is the number 2 or 3 and
x has a value from 1 to 6.

Examples of such compounds are the reaction products of n-butyltriglycolamine of the formula $H_2N$—$(CH_2$—$CH_2$—$O)_3$—$C_4H_9$ with methyl dodecanoate, or the reaction products of ethyltetraglycolamine of the formula $H_2N$—$(CH_2$—$CH_2$—$O)_4$—$C_2H_5$ with a commercially available mixture of saturated $C_8$-to $C_{18}$-fatty acid methyl esters.

Further suitable nonionic surfactants are also block copolymers of ethylene oxide, propylene oxide and/or butylene oxide (Pluronic® and Tetronic® grades from BASF), polyhydroxy or polyalkoxy fatty acid derivatives, such as polyhydroxy fatty acid amides, N-alkoxy- or N-aryloxy-polyhydroxy fatty acid amides, fatty acid amide ethoxylates, in particular those which are terminally capped, and fatty acid alkanolamide alkoxylates.

The additional nonionic surfactants are preferably present in the detergents and cleaners according to the invention in an amount of from 0.01 to 30% by weight, in particular 0.1 to 25% by weight, especially 0.5 to 20% by weight.

It is possible to use individual nonionic surfactants or a combination of different nonionic surfactants. It is possible to use nonionic surfactants from just one class, in particular only alkoxylated $C_8$–$C_{22}$-alcohols, but it is also possible to use surfactant mixtures from different classes.

Suitable anionic surfactants are, for example, fatty alcohol sulfates of fatty alcohols having 8 to 22, preferably 10 to 18, carbon atoms, e.g. $C_9$–$C_{11}$-alcohol sulfates, $C_{12}$–$C_{14}$-alcohol sulfates, $C_{12}$–$C_{18}$-alcohol sulfates, lauryl sulfate, cetyl sulfate, myristyl sulfate, palmityl sulfate, stearyl sulfate and tallow fatty alcohol sulfate.

Further suitable anionic surfactants are sulfated ethoxylated $C_8$–$C_{22}$-alcohols (alkyl ether sulfates) or soluble salts thereof. Compounds of this type are prepared, for example, by firstly alkoxylating a $C_8$- to $C_{22}$-alcohol, preferably a $C_{10}$–$C_{18}$-alcohol, e.g. a fatty alcohol, and then sulfating the alkoxylation product. For the alkoxylation, preference is given to using ethylene oxide, 1 to 50 mol, preferably 1 to 20 mol, of ethylene oxide being used per mole of alcohol. The alkoxylation of the alcohols can, however, also be carried out with propylene oxide alone and optionally butylene oxide. Also suitable are those alkoxylated $C_8$–$C_{22}$-alcohols which contain ethylene oxide and propylene oxide or ethylene oxide and butylene oxide or ethylene oxide and propylene oxide and butylene oxide. The alkoxylated $C_8$–$C_{22}$-alcohols can contain the ethylene oxide, propylene oxide and butylene oxide units in the form of blocks or in random distribution. It is possible to obtain alkyl ether sulfates having a broad or narrow alkylene oxide homolog distribution depending on the type of alkoxylation catalyst.

Further suitable anionic surfactants are alkanesulfonates, such as $C_8$–$C_{24}$-alkanesulfonates, preferably $C_{10}$–$C_{18}$-alkanesulfonates, and soaps, for example the Na and K salts of $C_8$- to $C_{24}$-carboxylic acids.

Further suitable anionic surfactants are linear $C_8$–$C_{20}$-alkylbenzenesulfonates ("LAS"), preferably linear $C_9$- to $C_{13}$-alkylbenzenesulfonates and -alkyltoluenesulfonates.

Further suitable anionic surfactants are also $C_8$— to $C_{24}$-olefinsulfonates and -disulfonates, which can also be mixtures of alkene- and hydroxyalkanesulfonates or -disulfonates, alkyl ester sulfonates, sulfonated polycarboxylic acids, alkylglycerol sulfonates, fatty acid glycerol ester sulfonates, alkylphenol polyglycol ether sulfates, paraffinsulfonates having about 20 to about 50 carbon atoms (based on paraffin recovered from natural sources, or on paraffin mixtures), alkylphosphates, acylisethionates, acyltaurates, acylmethyltaurates, alkylsuccinic acids, alkenylsuccinic acids or monoesters or monoamides thereof, alkylsulfosuccinic acids or amides thereof, mono- and diesters of sulfosuccinic acids, acylsarcosinates, sulfated alkylpolyglucosides, alkylpolyglycolcarboxylates and hydroxyalkylsarcosinates.

The anionic surfactants are preferably added to the detergents and cleaners in the form of salts. Suitable cations in these salts are alkali metal ions, such as sodium, potassium and lithium and ammonium salts, such as hydroxyethylammonium, di(hydroxyethyl)ammonium and tri(hydroxyethyl) ammonium salts.

The anionic surfactants are present in the detergents according to the invention preferably in an amount of up to 30% by weight, for example from 0.1 to 30% by weight, especially 1 to 25% by weight, in particular 3 to 20% by weight. If $C_9$- to $C_{20}$-linear-alkylbenzene-sulfonates (LAS) are co-used, these are usually used in an amount up to 15% by weight, in particular up to 10% by weight.

In the cleaners the anionic surfactants are present according to the invention in an amount of up to 30% by weight, especially up to 25% by weight, in particular up to 15% by weight. If $C_9$- to $C_{20}$-linear-alkylbenzenesulfonates (LAS) are co-used, these are usually used in an amount up to 10% by weight, in particular up to 8% by weight.

It is possible to use individual anionic surfactants or a combination of different anionic surfactants. It is possible to use anionic surfactants from only one class, for example only fatty alcohol sulfates or only alkylbenzenesulfonates, although it is also possible to use surfactant mixtures from different classes, e.g. a mixture of fatty alcohol sulfates and alkylbenzenesulfonates. Also, the surfactants of the formula I to be used according to the invention can be combined with cationic surfactants, usually in an amount up to 25% by weight, preferably 0.1 to 15% by weight, for example $C_8$- to $C_{16}$-dialkyldimethylammonium halides, dialkoxydimethylammonium halides or imidazolinium salts with a long-chain alkyl radical; and/or with amphoteric surfactants, usually in an amount up to 15% by weight, preferably 0.1 to 10% by weight, for example derivatives of secondary or tertiary amines, such as $C_6$–$C_{18}$-alkylbetaines or $C_6$–$C_{15}$-alkylsulfobetaines or amine oxides, such as alkyldimethylamine oxides.

The surfactants of the formula I to be used according to the invention are usually combined with builders (sequestering agents), such as polyphosphates, polycarboxylates, phosphonates, complexing agents, e.g. methylglycinediacetic acid and salts thereof, nitrilotriacetic acid and salts thereof, ethylenediaminetetraacetic acid and salts thereof, and optionally with cobuilders.

Individual builder substances which are highly suitable for combination with the surfactants of the formula I to be used according to the invention may be listed below:

Suitable inorganic builders are primarily crystalline or amorphous alumosilicates having ion-exchange properties, such as, in particular, zeolites. Different types of zeolites are suitable, in particular zeolites A, X, B, P, MAP and HS in their Na form or in forms in which Na is partially exchanged for other cations, such as Li, K, Ca, Mg or ammonium. Suitable zeolites are described, for example, in U.S. Pat. No. 4,604,224.

Crystalline silicates which are suitable as builders are, for example, disilicates or phyllosilicates, e.g. δ-$Na_2Si_2O_5$ or β-$Na_2Si_2O_5$ (SKS 6 or SKS 7 respectively). The silicates can be used in the form of their alkali metal, alkaline earth metal or ammonium salts, preferably as Na, Li and Mg silicates. Amorphous silicates, such as, for example, sodium metasilicate, which has a polymeric structure, or amorphous disilicate (Britesil® H 20 manufacturer: Akzo) can likewise be used.

Suitable inorganic carbonate-based builder substances are carbonates and hydrogencarbonates. These can be used in the form of their alkali metal, alkaline earth metal or ammonium salts. Preference is given to using Na, Li and Mg carbonates or hydrogen carbonates, in particular sodium carbonate and/or sodium hydrogencarbonate.

Customary phosphates used as inorganic builders are alkali metal orthophosphates and/or polyphosphates, such as pentasodium triphosphate.

Said builder components can be used individually or in mixtures with one another.

In addition, in many cases it is expedient to add cobuilders to the detergents and cleaners according to the invention. Examples of suitable substances are listed below.

In a preferred embodiment, the detergents and cleaners according to the invention comprise, in addition to the inorganic builders, 0.05 to 20% by weight, in particular 1 to 10% by weight, of organic cobuilders in the form of low molecular weight, oligomeric or polymeric carboxylic acids, in particular polycarboxylic acids, or phosphonic acids or salts thereof, in particular Na or K salts.

Examples of low molecular weight carboxylic acids or phosphonic acids which are suitable as organic cobuilders are:

phosphonic acids, such as 1-hydroxyethane-1,1-diphosphonic acid, aminotris(methylenephosphonic acid), ethylenediaminetetra(methylenephosphonic acid), hexamethylenediaminetetra(methylenephosphonic acid) and diethylenetriaminepenta(methylenephosphonic acid);

$C_4$- to $C_{20}$-di-, -tri- and -tetracarboxylic acids, such as succinic acid, propanetricarboxylic acid, butanetetracarboxylic acid, cyclopentanetetracarboxylic acid and alkyl- and alkenylsuccinic acids having $C_2$- to $C_{16}$-alkyl or alkenyl radicals respectively;

$C_4$- to $C_{20}$-hydroxycarboxylic acids, such as malic acid, tartaric acid, gluconic acid, glutaric acid, citric acid, lactobionic acid and sucrosemono-, di- and tricarboxylic acid; aminopolycarboxylic acids, such as nitrilotriacetic acid, β-alaninediacetic acid, ethylene-diaminetetraacetic acid, serinediacetic acid, isoserinediacetic acid, alkyl ethylenediaminetri-acetate, N,N-bis(carboxymethyl) glutamic acid, ethylene-diaminedisuccinic acid and N-(2-hydroxyethyl)iminodiacetic acid, methyl- and ethylglycinediacetic acid.

Examples of oligomeric or polymeric carboxylic acids which are suitable as organic cobuilders are:

oligomaleic acids, as described, for example, in EP-A 451508 and EP-A 396303;

Co- and terpolymers of unsaturated $C_4$- to $C_8$-dicarboxylic acids, the copolymerized comonomers being monoethylenically unsaturated monomers from group (i), given below, in amounts of up to 95% by weight, from group (ii)

in amounts of up to 60% by weight and from group (iii) in amounts of up to 20% by weight.

Examples of unsaturated $C_4$- to $C_8$-dicarboxylic acids in this context are maleic acid, fumaric acid, itaconic acid and citraconic acid. Preference is given to maleic acid.

Group (i) includes monoethylenically unsaturated $C_3$–$C_8$-monocarboxylic acids, such as acrylic acid, methacrylic acid, crotonic acid and vinylacetic acid. From group (i), preference is given to using acrylic acid and methacrylic acid.

Group (ii) includes monoethylenically unsaturated $C_2$- to $C_{22}$-olefins, vinyl alkyl ethers having $C_1$- to $C_8$-alkyl groups, styrene, vinyl esters of $C_1$- to $C_8$-carboxylic acids, (meth) acrylamide and vinylpyrrolidone. From group (ii), preference is given to using $C_2$- to $C_6$-olefins, vinyl alkyl ethers having $C_1$- to $C_4$-alkyl groups, vinyl acetate and vinyl propionate.

If the polymers of group (ii) contain copolymerized vinyl esters, some or all of the latter can also be present in hydrolyzed form to give vinyl alcohol structural units. Suitable co- and terpolymers are known, for example, from U.S. Pat. No. 3,887,806 and DE-A 4313909.

Group (iii) includes (meth)acrylic esters of $C_1$- to $C_8$-alcohols, (meth)acrylonitrile, (meth)acrylamides of $C_1$- to $C_8$-amines, N-vinylformamide and N-vinylimidazole.

Also suitable as organic cobuilders are homopolymers of monoethylenically unsaturated $C_3$–$C_8$-monocarboxylic acids, such as acrylic acid, methacrylic acid, crotonic acid and vinylacetic acid, in particular acrylic acid and methacrylic acid, copolymers of dicarboxylic acids, such as copolymers of maleic acid and acrylic acid in the weight ratio 10:90 to 95:5, particularly preferably those in the weight ratio 30:70 to 90:10 having molar masses of from 1000 to 150,000;

terpolymers of maleic acid, acrylic acid and a vinyl ester of a $C_1$–$C_3$-carboxylic acid in the weight ratio 10 (maleic acid): 90 (acrylic acid+vinyl ester) to 95 (maleic acid): 10 (acrylic acid+vinyl ester), where the weight ratio of acrylic acid to the vinyl ester can vary within the range from 30:70 to 70:30;

copolymers of maleic acid with $C_2$–$C_8$-olefins in the molar ratio 40:60 to 80:20, copolymers of maleic acid with ethylene, propylene or isobutene in the molar ratio 50:50 being particularly preferred.

Graft polymers of unsaturated carboxylic acids onto low molecular weight carbohydrates or hydrogenated carbohydrates, cf. U.S. Pat. No. 5,227,446, DE-A 4415623 and DE-A 4313909, are likewise suitable as organic cobuilders.

Examples of suitable unsaturated carboxylic acids in this context are maleic acid, fumaric acid, itaconic acid, citraconic acid, acrylic acid, methacrylic acid, crotonic acid and vinylacetic acid, and mixtures of acrylic acid and maleic acid, which are grafted on in amounts of from 40 to 95% by weight, based on the component to be grafted.

For modification, it is additionally possible for up to 30% by weight, based on the component to be grafted, of further monoethylenically unsaturated monomers to be present in copolymerized form. Suitable modifying monomers are the abovementioned monomers of groups (ii) and (iii).

Suitable graft bases are degraded polysaccharides, such as acidically or enzymatically degraded starches, inulins or cellulose, protein hydrolysates and reduced (hydrogenated or reductively aminated) degraded polysaccharides, such as mannitol, sorbitol, aminosorbitol and N-alkylglucamine, and also polyalkylene glycols having molar masses up to $M_W$=5000, such as polyethylene glycols, ethylene oxide/propylene oxide or ethylene oxide/butylene oxide or ethylene oxide/propylene oxide/butylene oxide block copolymers and alkoxylated mono- or polyhydric $C_1$- to $C_{22}$-alcohols (cf. U.S. Pat. No. 5,756,456).

Polyglyoxylic acids suitable as organic cobuilders are described, for example, in EP-B-001004, U.S. Pat. No. 5,399,286, DE-A-4106355 and EP-A-656914. The end groups of the polyglyoxylic acids can have different structures.

Polyamidocarboxylic acids and modified polyamidocarboxylic acids suitable as organic cobuilders are known, for example, from EP-A-454126, EP-B-511037, WO-A-94/01486 and EP-A-581452.

In particular, polyaspartic acids or cocondensates of aspartic acid with further amino acids, $C_4$- to $C_{25}$-mono- or -dicarboxylic acids and/or $C_4$- to $C_{25}$-mono- or -diamines are also used as organic cobuilders. Particular preference is given to using polyaspartic acids which have been prepared in phosphorus-containing acids and modified with $C_6$- to $C_{22}$-mono- or -di-carboxylic acids or with $C_6$- to $C_{22}$-mono- or -diamines.

Also suitable as organic cobuilders are iminodisuccinic acid, oxydisuccinic acid, aminopolycarboxylates, alkylpolyaminocarboxylates, aminopolyalkylenephosphonates, polyglutamates, hydrophobically modified citric acid, such as agaric acid, poly-α-hydroxyacrylic acid, N-acyl ethylenediaminetriacetates, such as lauroyl ethylenediaminetriacetate, and alkylamides of ethylenediaminetetraacetic acid, such as EDTA-tallow amide.

Furthermore, it is also possible to use oxidized starches as organic cobuilders.

In a further preferred embodiment, the detergents and cleaners according to the invention additionally comprise, in particular in addition to the inorganic builders, the anionic surfactants and/or the nonionic surfactants, 0.5 to 20% by weight, in particular 1 to 10% by weight, of glycine-N,N-diacetic acid derivatives, as described in WO 97/19159.

It is also frequently expedient to add bleaching systems, consisting of bleaches, such as perborate, percarbonate, and optionally bleach activators, such as tetraacetylethylenediamine, +bleach stabilizers to the detergents and cleaners according to the invention.

In these cases, the detergents and cleaners according to the invention additionally comprise 0.5 to 30% by weight, in particular 5 to 27% by weight, especially 10 to 23% by weight, of bleaches in the form of percarboxylic acids, e.g. diperoxododecanedicarboxylic acid, phthalimidopercaproic acid or monoperoxophthalic acid or -terephthalic acid, adducts of hydrogen peroxide with inorganic salts, e.g. sodium perborate monohydrate, sodium perborate tetrahydrate, sodium carbonate perhydrate or sodium phosphate perhydrate, adducts of hydrogen peroxide with organic compounds, e.g. urea perhydrate, or of inorganic peroxo salts, e.g. alkali metal persulfates or -peroxodisulfates, optionally in combination with 0 to 15% by weight, preferably 0.1 to 15% by weight, in particular 0.5 to 8% by weight, of bleach activators.

Suitable bleach activators are:

polyacylated sugars, e.g. pentaacetylglucose;

acyloxybenzenesulfonic acids and alkali metal and alkaline earth metal salts thereof, e.g. sodium p-nonanoyloxybenzenesulfonate or sodium p-benzoyloxybenzenesulfonate;

N,N-diacylated and N,N,N',N'-tetraacylated amines, e.g. N,N,N',N'-tetraacetylmethylenediamine and -ethylenediamine (TAED), N,N-diacetylaniline, N,N-diacetyl-p- toluidine or 1,3-diacylated hydantoins, such as 1,3-diacetyl-5,5-dimethylhydantoin;

N-alkyl-N-sulfonylcarbonamides, e.g. N-methyl-N-mesylacetamide or N-methyl-N-mesylbenzamide;

N-acylated cyclic hydrazides, acylated triazoles or urazoles, e.g. monoacetylmaleic hydrazide;

O,N,N-trisubstituted hydroxylamines, e.g. O-benzoyl-N, N-succinylhydroxylamine, O-acetyl-N,N-succinylhydroxylamine or O,N,N-triacetylhydroxylamine;

N,N'-diacylsulfurylamides, e.g. N,N'-dimethyl-N,N'-diacetylsulfurylamide or N,N'-diethyl-N,N'-dipropionylsulfurylamide;

acylated lactams, for example acetylcaprolactam, octanoylcaprolactam, benzoylcaprolactam or carbonylbiscaprolactam;

anthranil derivatives, such as 2-methylanthranil or 2-phenylanthranil;

triacyl cyanurates, e.g. triacetyl cyanurate or tribenzoyl cyanurate;

oxime esters and bisoxime esters, such as O-acetylacetone oxime or bisisopropyliminocarbonate;

carboxylic anhydrides, e.g. acetic anhydride, benzoic anhydride, m-chlorobenzoic anhydride or phthalic anhydride;

enol esters, such as isopropenyl acetate;

1,3-diacyl-4,5-diacyloxyimidazolines, e.g. 1,3-diacetyl-4,5-diacetoxyimidazoline;

tetraacetylglycoluril and tetrapropionylglycoluril;

diacylated 2,5-diketopiperazines, e.g. 1,4-diacetyl-2,5-diketopiperazine;

ammonium-substituted nitriles, such as N-methylmorpholinium acetonitrile methylsulfate;

acylation products of propylene diurea and 2,2-dimethylpropylenediurea, e.g. tetraacetylpropylenediurea;

α-acyloxypolyacylmalonamides, e.g. α-acetoxy-N,N'-diacetylmalonamide;

diacyldioxohexahydro-1,3,5-triazines, e.g. 1,5-diacetyl-2,4-dioxohexahydro-1,3,5-triazine;

benz-(4H)-1,3-oxazin-4-ones having alkyl radicals, e.g. methyl, or aromatic radicals, e.g. phenyl, in the 2-position.

The described bleaching system comprising bleaches and bleach activators can optionally also comprise bleach catalysts. Examples of suitable bleach catalysts are the quaternized imines and sulfonimines which are described, for example, in U.S. Pat. No. 5,360,569 and EP-A 453 003. Particularly effective bleach catalysts are manganese complexes, which are described, for example, in WO-A 94/21777. Where used, such compounds are incorporated into the detergents and cleaners in amounts of at most 1.5% by weight, in particular up to 0.5% by weight, and in the case of very active manganese complexes, in amounts up to 0.1% by weight.

In addition to the described bleaching system comprising bleaches, bleach activators and optionally bleach catalysts, it is also possible to use systems having enzymatic peroxide release or photoactivated bleaching systems for the detergents and cleaners according to the invention.

For a number of uses, it is expedient for the detergents and cleaners according to the invention to comprise enzymes. Enzymes which are preferably used in detergents and cleaners are proteases, amylases, lipases and cellulases. Preferred amounts of the enzymes are from 0.1 to 1.5% by weight, particularly preferably 0.2 to 1.0% by weight, of the formulated enzyme. Examples of suitable proteases are Savinase and Esperase (manufacturer: Novo Nordisk). An example of a suitable lipase is Lipolase (manufacturer: Novo Nordisk).

An example of a suitable cellulase is Celluzym (manufacturer: Novo Nordisk). The use of peroxidases for activating the bleach system is also possible. It is possible to use individual enzymes or a combination of different enzymes. Where appropriate, the detergents and cleaners according to the invention can also comprise enzyme stabilizers, e.g. calcium propionate, sodium formate or boric acids or salts thereof, and/or antioxidants.

The constituents of detergents and cleaners are known in principle to a person skilled in the art. The lists, above and below, of suitable constituents give merely an illustrative selection of the known suitable constituents.

In addition to the skin components stated hitherto, the detergents and cleaners according to the invention can also comprise the following further customary additives in the amounts customary for this purpose:

known dispersants, such as naphthalenesulfonic acid condensates or polycarboxylates, pH-regulating compounds, such as alkalis or alkali donors (NaOH, KOH, pentasodium meta-silicate) and acids (hydrochloric acid, phosphoric acid, amidosulfuric acid, citric acid), buffer systems, such as acetate or phosphate buffer, perfume, dyes, biocides, such as isothiazolinones or 2-bromo-2-nitro-1,3-propanediol, solubilizers/hydrotropic agents, such as cumenesulfonates, toluenesulfonates, short-chain fatty acids, urea, alcohols or phosphoric alkyl/aryl esters, alkyl/aryl polyglycol phosphoric esters, foam regulators for stabilizing or suppressing foam, skin protectants and corrosion inhibitors, disinfecting compounds or systems, such as those which liberate chlorine or hypochlorous acid, such as dichloroisocyanurate, or which comprise iodine.

Detergents may further contain soil-suspending agents, soil release agents, such as e.g. polyether esters, encrustation inhibitors, ion exchangers, antiredeposition inhibitors, optical (fluorescent) brighteners, color transfer inhibitors, such as e.g. polyvinylpyrrolidone, thickeners and extenders and formulating agents.

Cleaners may additionally contain solvents, such as short-chain alkyl oligoglycols, such as butyl glycol, butyl diglycol, propylene glycol monomethyl ether, alcohols, such as ethanol, isopropanol, aromatic solvents, such as toluene, xylene, N-alkylpyrrolidones or alkylene carbonates, thickeners, such as polysaccharides, and/or weakly crosslinked polycarboxylates (for example Carbopol® from Goodrich), finely divided abrasive components, such as quartz or marble powder, chalk, diatomaceous earth, pumice or else polishing rouge or emery.

The detergents are usually, but not exclusively, in solid, pulverulent form, and then usually additionally comprise customary extenders which impart good flowability, dosability and solubility thereto and which prevent caking and dusting, such as e.g. sodium sulfate or magnesium sulfate.

The pulverulent detergents have, in the customary form, an average bulk weight of about 450 g/l. Compact and ultracompact detergents and extrudates have a bulk weight of >600 g/l. These are becoming more and more important.

If they are to be used in liquid form, they can be in the form of aqueous microemulsions, emulsions or solutions. In liquid detergents it is possible to additionally use solvents such as e.g. ethanol, isopropanol, 1,2-propylene glycol or diethylene glycol butyl ether.

If the detergents according to the invention are in gel form, thickeners, such as e.g. polysaccharides and/or weakly crosslinked polycarboxylates (for example Carbopol® from Goodrich) may additionally be used.

In the case of detergents in tablet form, tableting auxiliaries, such as polyethylene glycols having molar masses of >1000 g/mol, polymer dispersions, and tablet disintegrants, such as cellulose derivatives, crosslinked polyvinylpyrrolidone, crosslinked polyacrylates or combinations of acids, e.g. citric acid+sodium bicarbonate, to name but a few, are additionally required.

The cleaners are usually, but not exclusively, aqueous and are in the form of micro-emulsions, emulsions or solutions.

If they are to be in solid, pulverulent form, customary extenders, which impart good flowability, dosability and solubility and/or which prevent agglomeration and dusting, such as sodium sulfate or magnesium sulfate, can additionally be used.

In the case of cleaners in tablet form, tableting auxiliaries, such as polyethylene glycols having molar masses of >1000 g/mol, polymer dispersions, and tablet disintegrants, such as cellulose derivatives, crosslinked polyvinylpyrrolidone, crosslinked polyacrylates or combinations of acids, e.g. citric acid+sodium bicarbonate, to name but a few, are additionally required.

Surprisingly, the detergents and cleaners according to the invention are considerably superior in terms of their cleaning action to the closest comparable detergents and cleaners. As the comparison carried out within the framework of the working examples shows, they have considerable advantages in terms of cleaning performance over the known $C_{13}$-oxo alcohol surfactants prepared on the basis of trimerized butenes.

The present invention further provides a process for the preparation of detergents and cleaners in which surfactants of the formula I are used.

The invention also provides for a washing process employing a detergent according to the invention and for the use of cleaners according to the invention for the cleaning of continuous, preferably hard, surfaces.

Of prime importance for the surprisingly high effectiveness of the surfactants of the formula I used according to the invention over the closest comparable compounds is evidently the structure of the $C_aH_{2a+1}O$— radical.

This surprisingly effective structure of the surfactants to be used according to the invention is obtained if they are prepared by
a) subjecting a $C_4$-olefin mixture to metathesis,
b) separating off olefins having 5 and 6 carbon atoms from the metathesis mixture,
c) subjecting the separated-off olefins individually or in a mixture to a dimerization to give olefin mixtures having 10 to 12 carbon atoms,
d) subjecting the resulting olefin mixture, optionally after fractionation, to derivatization to give a mixture of oxo alcohols (surfactant alcohols) and
e) optionally alkoxylating the resulting oxo alcohols,
f) where appropriate, converting the oxo alcohols or oxo alcohol alkoxylates obtained in preparation steps d) or e) into the acidic sulfuric or phosphoric esters.

FIG. 1 illustrates this synthesis route to give the surfactants of the formula I to be used according to the invention.

The fundamentals of the metathesis used in process step a) have been described, for example, in Ullmann's Encyclopedia of Industrial Chemistry, 5$^{th}$ Edition, Volume A18, p. 235/236. Further information for carrying out the process is given, for example, in K. J. Ivin, "Olefin Metathesis", Academic Press, London, (1983); Houben-Weyl, E18, 1163–1223; R. L. Banks, Discovery and Development of Olefin Disproportionation, CHEMTECH (1986), February, 112–117.

If the metathesis is applied to the main constituents but-1-ene and but-2-ene present in the $C_4$-olefin streams, in the presence of suitable catalysts, olefins having 5 to 10 carbon atoms, preferably having 5 to 8 carbon atoms, but in particular pent-2-ene and hex-3-ene, are formed.

Suitable catalysts are, preferably, molybdenum, tungsten or rhenium compounds. It is particularly expedient to carry out the reaction under heterogeneous catalysis, the catalytically effective metals being used, in particular, in conjunction with $Al_2O_3$ or $SiO_2$ supports. Examples of such catalysts are $MoO_3$ or $WO_3$ on $SiO_2$, or $Re_2O_7$ on $Al_2O_3$.

It is particularly favorable to carry out the metathesis in the presence of a rhenium catalyst since in this case particularly mild reaction conditions are possible. For example, the metathesis can in this case be carried out at a temperature of from 0 to 50° C. and at low pressures of from about 0.1 to 0.2 MPa.

The dimerization of the olefins or olefin mixtures obtained in the metathesis stage gives dimerization products which, with regard to the further processing on surfactant alcohols, have particularly favorable components and a particularly advantageous composition, if a dimerization catalyst is used which comprises at least one element of subgroup VIII of the Periodic Table of the Elements.

Further, it is preferred to choose the catalyst composition and the reaction conditions such that a dimer mixture is obtained which comprises <10% by weight of compounds which have a structural element of the formula I (vinylidene group)

(I)

in which $A^1$ and $A^2$ are aliphatic hydrocarbons.

For the dimerization, preference is given to using the internal, linear pentenes and hexenes present in the metathesis product. Particular preference is given to the use of 3-hexene.

The dimerization can be carried out with homogeneous catalysis or heterogeneous catalysis. Preference is given to the heterogeneous procedure since here, firstly, catalyst removal is simplified and the process is thus more economical and, secondly, no environmentally harmful waste water is produced, as is usually produced during the removal of dissolved catalysts, for example by hydrolysis. A further advantage of the heterogeneous process is that the dimerization product does not contain halogens, in particular chlorine or fluorine. Homogeneously soluble catalysts generally contain halide-containing ligands or they are used in combination with halogen-containing cocatalysts. Halogen can be incorporated from such catalyst systems into the dimerization products, which considerably impairs both the product quality and also the further processing, in particular the hydroformylation to give surfactant alcohols.

For the heterogeneous catalysis, combinations of oxides of metals from subgroup VIII with aluminum oxide on support materials of silicon oxides and titanium oxides, as are known, for example, from DE-A-43 39 713, are expediently used. The heterogeneous catalyst can be used in a fixed bed—then preferably in coarse form as 1 to 1.5 mm chips—or in suspended form (particle size 0.05 to 0.5 mm).

In the case of heterogeneous implementation, the dimerization is expediently carried out at temperatures of from 80 to 200° C., preferably from 100 to 180° C., under the pressure prevailing at the reaction temperature, optionally also under a protective gas at a pressure above atmospheric, in a closed system. To achieve optimal conversions, the reaction mixture is circulated repeatedly, a certain proportion of the circulating product being continuously removed from the system and replaced with starting material.

The dimerization produces mixtures of monounsaturated hydrocarbons, the components of which predominantly have a chain length twice that of the starting olefins.

The dimerization catalysts and the reaction conditions are expediently chosen within the scope of the above details such that at least 80% of the components of the dimerization mixture have one branch or two branches on neighboring carbon atoms in the area from one quarter to three quarters, preferably from one third to two thirds, of the chain length of their main chain.

A very characteristic feature of the olefin mixtures thus prepared is their high proportion—generally greater than 75%, in particular greater than 80%—of components containing branches, and the low proportion—generally below 25%, in particular below 20%—of unbranched olefins. A further characteristic is that at the branching sites of the main chain, predominantly groups having (y–4) and (y–5) carbon atoms are bonded, where y is the number of carbon atoms in the monomer used for the dimerization. The value (y–5)=0 means that no side chains are present.

In the case of the $C_{12}$-olefin mixtures thus prepared, the main chain preferably carries methyl or ethyl groups at the branching points.

The position of the methyl and ethyl groups on the main chain is likewise characteristic: in the case of monosubstitution, the methyl or ethyl groups are in the position P=(n/2)–m of the main chain, where n is the length of the main chain and m is the number of carbon atoms in the side groups, and in the case of disubstitution products, one substituent is in the position P and the other is on the adjacent carbon atom P+1. The proportions of monosubstitution products (single branching) in the olefin mixture prepared according to the invention are characteristically in total in the range from 40 to 75% by weight, and the proportions of double-branched components are in the range from 5 to 25% by weight.

We have also found that the dimerization mixtures can be further derivatized particularly well when the position of the double bond satisfies certain requirements. In these advantageous olefin mixtures, the position of the double bonds relative to the branches is such that the ratio of the "aliphatic" hydrogen atoms to "olefinic" hydrogen atoms is in the range $H_{aliph.}:H_{olefin.}=(2*n-0.5):0.5$ to $(2*n-1.9):1.9$, where n is the number of carbon atoms in the olefin obtained in the dimerization.

("Aliphatic" hydrogen atoms are defined as those which are bonded to carbon atoms which are not involved in any C=C double bond ($\pi$ bond), and "olefinic" hydrogen atoms are those bonded to a carbon atom which participates in a $\pi$ bond.)

Particular preference is given to dimerization mixtures in which the ratio $H_{aliph.}:H_{olefin.}=(2*n-1.0):1$ to $(2*n-1.6):1.6$.

The olefin mixtures thus prepared are firstly hydroformylated by reaction with carbon monoxide and hydrogen in the presence of suitable, preferably cobalt- or rhodium-containing, catalysts, to give surfactant alcohols (oxo alcohols), branched primary alcohols.

A good overview of the process of hydroformylation with further numerous literature references is given, for example, in the comprehensive article by Beller et al. in Journal of Molecular Catalysis, A104 (1995) 17–85 or in Ullmanns Encyclopedia of Industrial Chemistry, Vol. A5 (1986), page 217 ff., page 333, and the relevant literature references.

The comprehensive information given therein allows the person skilled in the art to hydroformylate even the branched olefins according to the invention. In this reaction, Co and hydrogen are added to olefinic double bonds, giving mixtures of aldehydes and alkanols according to the following reaction scheme:

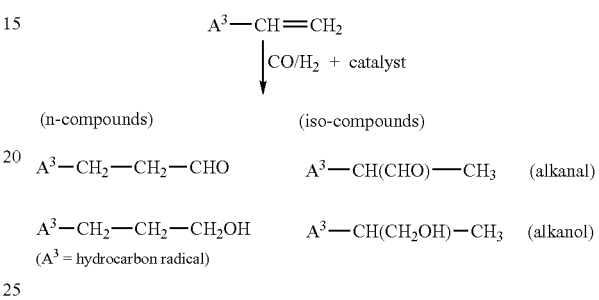

The molar ratio of n- and iso-compounds in the reaction mixture is usually in the range from 1:1 to 20:1 depending on the hydroformylation processing conditions chosen and the catalyst used. The hydroformylation is normally carried out in the temperature range from 90 to 200° C. and at a $CO/H_2$ pressure of from 2.5 to 35 MPa (25 to 350 bar). The mixing ratio of carbon monoxide to hydrogen depends on whether the intention is to produce alkanals or alkanols in preference. The CO:H is expediently in the range from 10:1 to 1:10, preferably 3:1 to 1:3, where, for the preparation of alkanals, the range of low hydrogen partial pressures is chosen, and for the preparation of alkanols the range of high hydrogen partial pressures is chosen, e.g. $CO:H_2=1:2$.

Suitable catalysts are predominantly metal compounds of the formula $HM(CO)_4$ or $M_2(CO)_8$, where M is a metal atom, preferably a cobalt, rhodium or ruthenium atom.

Generally, under hydroformylation conditions, the catalysts or catalyst precursors used in each case form catalytically active species of the formula $H_xM_y(CO)_zL_q$, in which M is a metal from subgroup VIII, L is a ligand which may be a phosphine, phosphite, amine, pyridine or any other donor compound, including in polymeric form, and q, x, y and z are integers depending on the valency and type of metal, and the covalence of the ligand L, where q can also be 0.

The metal M is preferably cobalt, ruthenium, rhodium, palladium, platinum, osmium or iridium and in particular cobalt, rhodium or ruthenium.

Suitable rhodium compounds or complexes are, for example, rhodium(II) and rhodium(III) salts, such as rhodium(III) chloride, rhodium(III) nitrate, rhodium(III) sulfate, potassium rhodium sulfate, rhodium(II) or rhodium(III) carboxylate, rhodium(II) and rhodium(III) acetate, rhodium(III) oxide, salts of rhodium(III) acid, such as trisammonium hexachlororhodate(III). Also suitable are rhodium complexes such as (acetylacetonato)dicarbonylrhodium(I), acetylacetonatobisethylenerhodium(I). Preference is given to using (acetylacetonato)dicarbonylrhodium(I) or rhodium acetate.

Examples of suitable cobalt compounds are cobalt(II) chloride, cobalt(II) sulfate, cobalt(II) carbonate, cobalt(II)

nitrate, amine or hydrate complexes thereof, cobalt carboxylates, such as cobalt acetate, cobalt ethylhexanoate, cobalt naphthanoate, and the cobalt caprolactamate complex. Here too it is possible to use the carbonyl complexes of cobalt, such as dicobalt octocarbonyl, tetracobalt dodecacarbonyl and hexacobalt hexadecacarbonyl.

Said compounds of cobalt, rhodium and ruthenium are known in principle and are adequately described in the literature, or they may be prepared by the person skilled in the art analogously to the compounds which are already known.

The hydroformylation can be carried out with the addition of inert solvents or diluents or without such an addition. Examples of suitable inert additives are acetone, methyl ethyl ketone, cyclohexanone, toluene, xylene, chlorobenzene, methylene chloride, hexane, petroleum ether, acetonitrile, and the high-boiling fractions from the hydroformylation of the dimerization products.

If the resulting hydroformylation product has too high an aldehyde content, this can be removed in a simple manner by hydrogenation, for example using hydrogen in the presence of Raney nickel or using other catalysts known for hydrogenation reactions, in particular catalysts containing copper, zinc, cobalt, nickel, molybdenum, zirconium or titanium. In the process, the aldehyde fractions are largely hydrogenated to give alkanols. A virtually residue-free removal of aldehyde fractions in the reaction mixture can, if desired, be achieved by afterhydrogenation, for example under particularly mild and economical conditions using an alkali metal borohydride.

Nonionic or anionic surfactants can be prepared from the alkanols thus prepared in various ways.

Nonionic surfactants are obtained by reacting the alkanols with alkylene oxides (alkoxylation) of the formula II

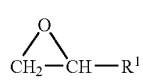
(II)

in which $R^1$ is hydrogen or a straight-chain or branched aliphatic radical of the formula $C_nH_{2n+1}$, and n is a number from 1 to 16, preferably from 1 to 8. In particular, $R^1$ is hydrogen, methyl, ethyl or propyl.

The alkanols according to the invention can be reacted with a single alkylene oxide species or with two or more different species. The reaction of the alkanols with the alkylene oxides produces compounds which in turn carry an OH group and can therefore react afresh with one molecule of alkylene oxide. Therefore, depending on the molar ratio of alkanol to alkylene oxide, reaction products are obtained which have polyether chains of varying length. The polyether chains can contain 1 to about 200 alkylene oxide structural groups. Preference is given to compounds whose polyether chains contain 1 to 50 alkylene oxide structural groups.

The chains can consist of identical chain members, or they can have different alkylene oxide structural groups which differ from one another by virtue of their radical $R^1$. These various structural groups can be present within the chain in random distribution or in the form of blocks.

The reaction scheme below serves to illustrate the alkoxylation of the above-described alkanols using the example of a reaction with two different alkylene oxides used in varying molar amounts x and y.

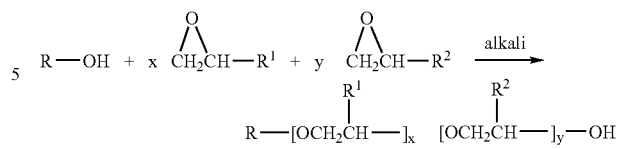

$R^1$ and $R^2$ are different radicals within the scope of the definitions given above for $R^1$, and R—OH is an above-described branched oxo alcohol.

The alkoxylation is preferably catalyzed by strong bases, which are expediently added in the form of an alkali metal hydroxide or alkaline earth metal hydroxide, usually in an amount of from 0.1 to 1% by weight, based on the amount of alkanol $R^2$—OH. (cf. G. Gee et al., J. Chem. Soc. (1961), p. 1345; B. Wojtech, Makromol. Chem. 66, (1966), p. 180).

Acidic catalysis of the addition reaction is also possible. As well as Bronsted acids, Lewis acids, such as $AlCl_3$ or $BF_3$, are also suitable. (cf. P.H. Plesch, The Chemistry of Cationic Polymerization, Pergamon Press, New York (1963)).

The addition reaction is carried out at temperatures of from about 120 to about 220° C., preferably from 140 to 160° C., in a sealed vessel. The alkylene oxide or the mixture of different alkylene oxides is introduced into the mixture of alkanol mixture according to the invention and alkali under the vapor pressure of the alkylene oxide mixture prevailing at the chosen reaction temperature. If desired, the alkylene oxide can be diluted by up to 30 to 60% with an inert gas. This leads to additional security against explosion-like polyaddition of the alkylene oxide.

If an alkylene oxide mixture is used, then polyether chains are formed in which the various alkylene oxide building blocks are distributed in virtually random manner. Variations in the distribution of the building blocks along the polyether chain arise due to varying reaction rates of the components and can also be achieved arbitrarily by continuous introduction of an alkylene oxide mixture of a program-controlled composition. If the various alkylene oxides are reacted successively, polyether chains having block-like distribution of the alkylene oxide building blocks are obtained.

The length of the polyether chains varies within the reaction product in a random manner about a mean, which essentially corresponds to the stoichiometric value arising from the amount added.

The alkanol mixtures originating from the synthesis step d) and also the polyethers optionally prepared therefrom in synthesis step e) can be converted into anionic surfactants by esterification in a manner known per se with sulfuric acid or sulfuric acid derivatives to give acidic alkylsulfates or alkyl ether sulfates, or with phosphoric acid or its derivatives to give acidic alkylphosphates or alkyl ether phosphates (sulfation or phosphation).

Sulfation reactions of alcohols have already been described, e.g. in U.S. Pat. Nos. 3,462,525, 3,420,875 or 3,524,864. Details on carrying out this reaction are also given in "Ullmanns Encyclopedia of Industrial Chemistry", $5^{th}$ edition, vol. A25 (1994), pages 779–783 and in the literature references cited therein.

If sulfuric acid itself is used for the esterification, then a 75 to 100% strength by weight, preferably 85 to 98% strength by weight, acid is expediently used (so-called "concentrated sulfuric acid" or "monohydrate"). The esterification can be carried out in a solvent or diluent if desired for control of the reaction, e.g. evolution of heat. The usual procedure involves introducing the alcoholic reactant and gradually adding the sulfating agent with continuous thorough mixing. If complete esterification of the alcohol component is desired, the sulfating agent and the alkanol are used in the molar ratio from 1:1 to 1:1.5, preferably from 1:1 to 1:1.2. Lesser amounts of sulfating agents can be advantageous if mixtures of alkanol alkoxylates according to the invention are used and if the intention is to prepare combinations of neutral and anionic surfactants. The esterification is normally carried out at temperatures of from room temperature to 85° C., preferably in the range from 45 to 75° C.

Where appropriate, it may be expedient to carry out the esterification in a low-boiling, water-immiscible solvent or diluent at its boiling point, the water which forms during the esterification being distilled off azeotropically.

For the sulfation of the alkanol mixtures according to the invention, instead of sulfuric acid of the above concentration, it is also possible to use, for example, sulfur trioxide, sulfur trioxide complexes, solutions of sulfur trioxide in sulfuric acid ("oleum"), chlorosulfonic acid, sulfuryl chloride and also amidosulfonic acid. The reaction conditions must then be adapted appropriately.

If sulfur trioxide is used as sulfating agent, then the reaction may also advantageously be carried out in a falling-film reactor in countercurrent, if desired also continuously.

Following esterification, the mixtures are neutralized by adding alkali and, optionally following the removal of excess alkali metal sulfate and any solvent present, are worked up.

In an analogous way, alkanols and alkanol ethers and mixtures thereof can also be reacted with phosphating agents (phosphated) to give acidic phosphoric esters.

Suitable phosphating agents are primarily phosphoric acid, polyphosphoric acid and phosphorus pentoxide, but also $POCl_3$, if hydrolysis of the remaining acid chloride functions is subsequently undertaken. The phosphation of alcohols has been described, for example, in Synthesis 1985, pages 449 to 488.

The working examples below illustrate the preparation and use of the surfactants to be used according to the invention.

EXAMPLE 1

Preparation of $C_5/C_6$-olefins from $C_4$-olefin Streams by Metathesis

A butadiene-free $C_4$ fraction having a total butene content of 84.2% by weight and a 1-butene: 2-butene molar ratio of 1.06 ("raffinate II") is passed continuously at 40° C. and 10 bar through a tubular reactor charged with $Re_2O_7/Al_2O_3$ heterogeneous catalyst. The space velocity is adjusted to 4500 kg/(m²*h). The reactor discharge is separated by distillation and comprises the following components (data in mass percent):

ethene: 1.15%, propene: 18.9%, butane: 15.8%, 2-butene: 19.7%, 1-butene: 13.3%, iso-butene: 1.00%, 2-pentene: 19.4%, methylbutene: 0.45%, 3-hexene 10.3%.

EXAMPLES 2A AND 2B

Heterogeneously Catalyzed Dimerization of 3-hexene

2A. Fixed-bed Procedure

An isothermally heatable reactor having a diameter of 16 mm was charged with 100 ml of a catalyst of the following composition:

50% by weight of NiO, 34% by weight of $SiO_2$, 13% by weight of $TiO_2$, 3% by weight of $Al_2O_3$ (as in DE-A-43 39 713), conditioned for 24 h at 160° C. in $N_2$ used as 1 to 1.5 mm chips.

5 experiments were carried out, 3-hexene (99.9% pure by weight, 0.1% by weight of $C_7$ to $C_{11}$ fractions) being passed through the fixed catalyst bed at a rate (WHSV), based on the reactor volume, of 0.25 kg/l*h, and removed from the system at a rate of from 24 to 28 g/h. The parameters varied in the individual experiments were the reaction temperature and the operating time of the experiment.

Table 1 below shows the experimental conditions of the five experiments and the results obtained therein.

TABLE 1

| Process conditions and results for the fixed-bed process | | | | | | |
|---|---|---|---|---|---|---|
| Reaction conditions | | | | | | |
| Temperature [° C.] | 100 | 120 | 140 | 160 | 160 | $C_{12}$ distillate |
| Pressure [bar] | 20 | 20 | 20 | 25 | 25 | |
| Operating hours | 12 | 19 | 36 | 60 | 107 | |
| Liquid produced [g/h] | 24 | 27 | 27 | 28 | 27 | |
| Composition % by weight | | | | | | |
| $C_6$ | 68.5 | 52.7 | 43.6 | 57.0 | 73.2 | 0.1 |
| $C_7$–$C_{11}$ | 0.2 | 0.2 | 0.3 | 0.2 | 0.2 | — |
| $C_{12}$ | 25.9 | 38.6 | 44.0 | 35.6 | 23.6 | 99.9 |
| >$C_{12}$ | 5.4 | 8.5 | 12.1 | 7.2 | 3.0 | — |
| Conversion | 31.4 | 47.2 | 56.4 | 42.9 | 26.7 | — |
| $C_{12}$ selectivity [% by weight] | 82.5 | 81.8 | 78.2 | 83.0 | 88.4 | — |
| S content in the liquid produced [ppm] | — | — | — | — | — | — |

The removed product was fractionally distilled, and the backbone isomers of the $C_{12}$ fraction were determined. Analysis revealed 14.2% by weight of n-dodecenes, 31.8% by weight of 5-methylundecenes, 29.1% by weight of 4-ethyldecenes, 6.6% by weight of 5,6-dimethyldecenes, 9.3% by weight of 4-methyl-5-ethylnonenes and 3.7% by weight of diethyloctenes.

B. Suspension Process (Fluidized Bed Process)

An isothermally heatable reactor with a diameter of 20 mm and a volume of 157 ml was charged with 30 g of a catalyst of the following composition:

50% by weight of NiO, 34% by weight of $SiO_2$, 13% by weight of $TiO_2$, 3% by weight of $Al_2O_3$ (as in DE-A-43 39 713), conditioned for 24 h at 160° C. in $N_2$, used as 0.05 to 0.5 mm spray material.

6 experiments were carried out, 3-hexene (99.9% pure by weight, 0.1% by weight of $C_7$ to $C_{11}$ fractions) being passed through the catalyst fluidized bed from below at a rate, based on the reactor volume, of 0.25 kg/l*h. Most of the reaction product leaving the reactor was recycled (recycling: feed amount varied between about 45 and 60). The parameters which were varied in the individual experiments were also the reaction temperature, the feed amount, the circulation stream, the recycle rate and the WHSV of the experiment. The experiment duration was 8 hours.

Tables 2A and 2B below show the experimental conditions of the six experiments and the results obtained therein.

Tables 2

Experimental conditions and results for the suspension process.

TABLE 2A

Experimental conditions

| Experiment No. | Temperature [° C.] | Pressure [bar] | Feed [g/h] | Circulation [g/h] | Recycle rate [X:1] | WHSV | Operating time [h] |
|---|---|---|---|---|---|---|---|
| 1 | 130 | 11.0 | 20 | 1200 | 60.0 | 0.127 | 8 |
| 2 | 130 | 11.0 | 23 | 1200 | 52.2 | 0.146 | 8 |
| 3 | 130 | 12.0 | 21 | 1100 | 52.4 | 0.134 | 8 |
| 4 | 130 | 12.2 | 24 | 1100 | 45.8 | 0.153 | 8 |
| 5 | 140 | 13.4 | 23 | 1180 | 51.3 | 0.146 | 8 |
| 6 | 150 | 14.1 | 22 | 1200 | 54.5 | 0.140 | 8 |

TABLE 2B

Composition of the reaction discharge

| Experiment No. | % $C_6$ | % > $C_6$ | % $C_{12}$ | % $C_{18}$ | % $C_{24}$ | % conversion | % $C_{12}$ selectivity |
|---|---|---|---|---|---|---|---|
| 1 | 83.9 | 0.5 | 14.3 | 1.1 | 0.2 | 16.1 | 88.82 |
| 2 | 80.5 | 0.5 | 16.9 | 1.8 | 0.3 | 19.5 | 86.67 |
| 3 | 80.3 | 0.4 | 17.0 | 1.9 | 0.3 | 19.7 | 86.29 |
| 4 | 81.6 | 0.5 | 15.5 | 2.0 | 0.3 | 18.4 | 84.24 |
| 5 | 75.9 | 0.5 | 20.4 | 2.6 | 0.5 | 24.1 | 84.65 |
| 6 | 71.1 | 0.6 | 24.0 | 3.5 | 0.7 | 28.9 | 83.04 |

The removed product was fractionally distilled and the backbone isomers of the $C_{12}$ fraction were determined. Analysis revealed 14% by weight of n-dodecenes, 32% by weight of 5-methylundecenes, 29% by weight of 4-ethyldecenes, 7% by weight of 5,6-dimethyldecenes, 9% by weight of 4-methyl-5-ethylnonenes and 4% by weight of diethyloctenes.

EXAMPLE 3

Hydroformylation of a Dodecene Mixture 750 g of the dodecene mixture prepared as in Example 2B are hydroformylated with 3.0 g 15 of $Co_2(CO)_8$ at 185° C. and 280 bar of $CO/H_2$ (volume ratio=1:1.5) with the addition of 75 g of $H_2O$ in a 2.5 l autoclave with lifter-stirrer for 5 hours. Cobalt is removed oxidatively from the reaction discharge using 10% strength by weight acetic acid with the introduction of air at 90° C. The oxo product is hydrogenated with the addition of 10% by weight of water in a 2.5 l autoclave with lifter-stirrer containing 50 g of Raney nickel at 125° C. and a hydrogen pressure of 280 bar for 10 hours. The reaction discharge is fractionally distilled.

450 g of a tridecanol fraction prepared in this way are afterhydrogenated with 3.5 g of $NaBH_4$.

The OH number of the resulting tridecanol is 277 mg of KOH/g.

Using $^1$H-NMR spectroscopy, a mean degree of branching of 2.3 methyl groups/molecule was determined, corresponding to a degree of branching of 1.3.

EXAMPLE 3A

Hydroformylation of a Dodecene Mixture 2.12 kg of the dodecene mixture prepared as in Example 2A are hydroformylated with 8 g of $Co_2(CO)_8$ at 185° C. and 280 bar of $CO/H_2$ (volume ratio 1:1) with the addition of 210 g of water in a 5 l autoclave fitted with rotary stirrer for 5 hours. Cobalt is oxidatively removed from the reaction discharge using 10% strength by weight acetic acid with the introduction of air at 90° C. The oxo product obtained is hydrogenated in a 5 l tubular reactor in trickle mode over a Co/Mo fixed-bed catalyst at 175° C. and a hydrogen pressure of 280 bar with the addition of 10% by weight of water. The alcohol mixture is worked up by distillation. The resulting tridecanol has an OH number of 279 mg of KOH/g; using $^1$H-NMR spectroscopy, a mean degree of branching of 1.53 is measured.

EXAMPLE 3B

Hydroformylation of a Dodecene Mixture 50 mg of rhodium biscarbonylacetylacetonate, 4.5 g of a polyethyleneimine of molar mass $M_W$=460,000, in which 60% of all nitrogen atoms have been acylated with lauric acid, 800 g of a dodecene mixture prepared as in Example 2A and 196 g of toluene are heated to 150° C. in a 2.5 l autoclave with lifter-stirrer under a pressure of 280 bar of $CO/H_2$ (volume ratio 1:1) for 7 hours. The autoclave is then cooled, decompressed and emptied. Gas chromatography of the reaction product obtained reveals an olefin conversion of 93%. The resulting oxo product is hydrogenated in a 2.5 l tubular reactor in trickle mode over a Co/Mo fixed-bed catalyst at 175° C. and a hydrogen pressure of 280 bar with the addition of 10% by weight of water, and the resulting alcohol mixture is worked up by distillation. The resulting tridecanol has an OH number of 279 mg of KOH/g; using $^1$H-NMR spectroscopy, a mean degree of branching of 1.63 is measured.

EXAMPLE 3C

Hydroformylation of a Dodecene Mixture 50 mg of rhodium biscarbonylacetylacetonate, 4.5 g of a polyethyleneimine of molar mass $M_W$=460,000, in which 60% of all nitrogen atoms have been acylated with lauric acid, 800 g of a dodecene mixture prepared as in Example 2A and 196 g of toluene are heated to 160° C. in a 2.5 l autoclave with lifter-stirrer under a pressure of 280 bar of $CO/H_2$ (volume ratio 1:1) for 7 hours. The autoclave is then cooled, decompressed and emptied. Gas chromatography of the reaction product obtained reveals an olefin conversion of 94%. The resulting oxo product is hydrogenated in a 2.5 l tubular reactor in trickle mode over a Co/Mo fixed-bed catalyst at 175° C. and a hydrogen pressure of 280 bar with the addition of 10% by weight of water, and the resulting alcohol mixture is worked up by distillation. The resulting tridecanol has an OH number of 279 mg of KOH/g; using $^1$H-NMR spectroscopy, a mean degree of branching of 1.69 is measured.

EXAMPLE 4

Preparation of a $C_{13}$-oxo Alcohol Ethoxylate with 2.75 mol of Ethylene Oxide 500 g of $C_{13}$-oxo alcohol (prepared as in Example 3B) are introduced with 1.2 g of NaOH into a dry 2 l autoclave. The autoclave contents are heated to 150° C. and 300 g of ethylene oxide are injected into the autoclave with pressure. After all of the ethylene oxide has been introduced into the autoclave, the autoclave is maintained at 150° C. for 30 minutes. After cooling, the catalyst is neutralized with acetic acid.

The resulting surfactant has a cloud point of 35° C., measured at 1% strength in a 10% strength solution of diethylene glycol butyl ether in accordance with DIN 53917. The surface tension at a concentration of 1 g/l is 25.8 mN/m, measured in accordance with DIN 53914.

EXAMPLE 5

Preparation of a $C_{13}$-oxo Alcohol Ethoxylate with 5 mol of Ethylene Oxide 400 g of $C_{13}$-oxo alcohol (prepared as in Example 3B) are introduced with 1.5 g of NaOH into a dry 2 l autoclave. The autoclave contents are heated to 150° C. and 440 g of ethylene oxide are injected into the autoclave with pressure. After all of the ethylene oxide has been introduced into the autoclave, the autoclave is maintained at 150° C. for 30 minutes. After cooling, the catalyst is neutralized with acetic acid.

The resulting surfactant has a cloud point of 58.5° C., measured at 1% strength in a 10% strength solution of diethylene glycol butyl ether in accordance with DIN 53917. The surface tension at a concentration of 1 g/l is 26.7 mN/m, measured in accordance with DIN 53914.

EXAMPLE 6

Preparation of a $C_{13}$-oxo Alcohol Ethoxylate with 7.5 mol of Ethylene Oxide 600 g of $C_{13}$-oxo alcohol (prepared as in Example 3B) are introduced with 1.6 g of NaOH into a dry 2 l autoclave. The autoclave contents are heated to 140° C. and 990 g of ethylene oxide are injected into the autoclave with pressure. After all of the ethylene oxide has been introduced into the autoclave, the autoclave is maintained at 140° C. for 40 minutes. After cooling, the catalyst is neutralized with acetic acid.

The resulting surfactant has a cloud point of 74° C., measured at 1% strength in a 10% strength solution of diethylene glycol butyl ether in accordance with DIN 53917. The surface tension at a concentration of 1 g/l is 26.6 mN/m, measured in accordance with DIN 53914.

EXAMPLE 7

Preparation of a $C_{13}$-oxo Alcohol Ethoxylate with 9.5 mol of Ethylene Oxide 300 g of $C_{13}$-oxo alcohol (prepared as in Example 3B) are introduced with 1.8 g of NaOH into a dry 2 l autoclave. The autoclave contents are heated to 150° C. and 630 g of ethylene oxide are injected into the autoclave with pressure. After all of the ethylene oxide has been introduced into the autoclave, the autoclave is maintained at 150° C. for 50 minutes. After cooling, the catalyst is neutralized with acetic acid.

The resulting surfactant has a cloud point of 66° C., measured at 1% strength in water in accordance with DIN 53917. The surface tension at a concentration of 1 g/l is 27.9 mN/m, measured in accordance with DIN 53914.

EXAMPLE 8

Preparation of a $C_{13}$-oxo Alcohol Ethoxylate with 2 mol of Ethylene Oxide 500 g of $C_{13}$-oxo alcohol (prepared as in Example 3B) are introduced with 1.0 g of NaOH into a dry 2 l autoclave. The autoclave contents are heated to 120° C. and 220 g of ethylene oxide are injected into the autoclave with pressure. After all of the ethylene oxide has been introduced into the autoclave, the autoclave is maintained at 120° C. for 30 minutes. After cooling, the catalyst is neutralized with sulfuric acid.

The resulting surfactant has a cloud point of 21° C., measured at 1% strength in a 10% strength solution of diethylene glycol butyl ether in accordance with DIN 53917. The surface tension at a concentration of 1 g/l is 26.6 mN/m, measured in accordance with DIN 53914.

EXAMPLE 9

(Comparison) Preparation of a $C_{13}$-oxo Alcohol Ethoxylate with 2.75 mol of Ethylene Oxide 500 g of $C_{13}$-oxo alcohol (prepared by trimerization of n-butenes and subsequent hydroformylation) are introduced together with 1.2 g of NaOH into a dry 2 l autoclave. The autoclave contents are heated to 150° C., and 300 g of ethylene oxide are injected into the autoclave under pressure. After all of the ethylene oxide has been introduced into the autoclave, the autoclave is maintained at 150° C. for 30 minutes. After cooling, the catalyst is neutralized with acetic acid.

The resulting surfactant has a cloud point of 39.5° C., measured at 1% strength in a 10% strength solution of diethylene glycol butyl ether in accordance with DIN 53917. The surface tension at a concentration of 1 g/l is 26.7 mN/m, measured in accordance with DIN 53914.

EXAMPLE 10

(Comparison) Preparation of a $C_{13}$-oxo Alcohol Ethoxylate with 5 mol of Ethylene Oxide 400 g of $C_{13}$-oxo alcohol (prepared by trimerization of n-butenes and subsequent hydroformylation) are introduced together with 1.5 g of NaOH into a dry 2 l autoclave. The autoclave contents are heated to 150° C., and 440 g of ethylene oxide are injected into the autoclave under pressure. After all of the ethylene oxide has been introduced into the autoclave, the autoclave is maintained at 150° C. for 30 minutes. After cooling, the catalyst is neutralized with acetic acid.

The resulting surfactant has a cloud point of 61° C., measured at 1% strength in a 10% strength solution of diethylene glycol butyl ether in accordance with DIN 53917. The surface tension at a concentration of 1 g/l is 27.2 mN/m, measured in accordance with DIN 53914.

EXAMPLE 11

(Comparison) Preparation of a $C_{13}$-oxo Alcohol Ethoxylate with 7 mol of Ethylene Oxide 400 g of $C_{13}$-oxo alcohol (prepared by trimerization of n-butenes and subsequent hydroformylation) are introduced together with 1.6 g of NaOH into a dry 2 l autoclave. The autoclave contents are heated to 150° C., and 440 g of ethylene oxide are injected into the autoclave under pressure. After all of the ethylene oxide has been introduced into the autoclave, the autoclave is maintained at 150° C. for 30 minutes. After cooling, the catalyst is neutralized with acetic acid.

The resulting surfactant has a cloud point of 70° C., measured at 1% strength in a 10% strength solution of diethylene glycol butyl ether in accordance with DIN 53917. The surface tension at a concentration of 1 g/l is 27.5 mN/m, measured in accordance with DIN 53914.

EXAMPLE 12

(Comparison) Preparation of a $C_{13}$-oxo Alcohol Ethoxylate with 9 mol of Ethylene Oxide 400 g of $C_{13}$-oxo alcohol (prepared by trimerization of n-butenes and subsequent hydroformylation) are introduced together with 1.7 g of NaOH into a dry 2 l autoclave.

The autoclave contents are heated to 150° C., and 440 g of ethylene oxide are injected into the autoclave under pressure. After all of the ethylene oxide has been introduced into the autoclave, the autoclave is maintained at 150° C. for 30 minutes. After cooling, the catalyst is neutralized with acetic acid.

The resulting surfactant has a cloud point of 60° C., measured at 1% strength in water in accordance with DIN 53917. The surface tension at a concentration of 1 g/l is 28.2 mN/m, measured in accordance with DIN 53914.

EXAMPLE 13

(Comparison) Preparation of a $C_{13}$-oxo Alcohol Ethoxylate with 9.7 mol of Ethylene Oxide 400 g of $C_{13}$-oxo alcohol prepared by trimerization of n-butenes and subsequent hydroformylation) are introduced together with 1.8 g of NaOH into a dry 2 l autoclave. The autoclave contents are heated to 150° C., and 440 g of ethylene oxide are injected into the autoclave under pressure. After all of the ethylene oxide has been introduced into the autoclave, the autoclave is maintained at 150° C. for 30 minutes. After cooling, the catalyst is neutralized with acetic acid.

The resulting surfactant has a cloud point of 70° C., measured at 1% strength in water in accordance with DIN 53917. The surface tension at a concentration of 1 g/l is 28.8 mN/m, measured in accordance with DIN 53914.

EXAMPLE 14

Washing Tests

The washing experiments were carried out in an LP 2 Launderometer from Atlas with the following formulation:

| | |
|---|---|
| 19% by weight | of surfactant |
| 30% by weight | of zeolite A |
| 12% by weight | of sodium carbonate |
| 3% by weight | of sodium silicate |
| 1.2% by weight | of carboxymethylcellulose (Tylose ® CR 1500p (based on active substance)) |
| 14.4% by weight | of sodium perborate monohydrate |
| 4% by weight | of TAED |
| 5% by weight | of polycarboxylate (Sokalan ® CP 5) |
| 0.5% by weight | of soap |
| 4% by weight | of sodium sulfate |
| 6.9% by weight | of water |
| Amount of detergent | 4 g/l |
| Liquor ratio | 12.5:1 |
| Water hardness | 3 mmol |
| Ca:Mg:$HCO_3^-$ | 4:18 |
| Wash time | 30 min |

The washing experiments were carried out using test material EMPA 101 (manufacturer: EMPA Testmaterials, Mövenstraβe 12, CH 9015 St. Gallen) and with test fabric wfk 10 D (manufacturer: wfk-Testgewebe GmbH, Christenfeld 10, 41375 Brueggen).

Soiling:

| | |
|---|---|
| EMPA 101: | soot/olive oil on cotton |
| wfk 10 D: | wfk pigment/sebum on cotton. |

The table below shows the results obtained in the washing experiments at 40° C. and at 60° C. The values given in each case are the degrees of reflectance in [%] of the irradiated amount of light, measured after the washing.

The degree of reflectance is measured using an Elrepho 2000 instrument from datacolor AG.

TABLE washing results

| | Wash temperature [° C.] | Degree of reflectance [%] in the case of EMPA 101 | Degree of reflectance [%] in the case of wfk 10 D |
|---|---|---|---|
| Example 4 | 40 | 31 | 59 |
| Example 5 | 40 | 28 | 51 |
| Example 6, (comparison) | 40 | 28 | 51 |
| Example 7, (comparison) | 40 | 26 | 51 |
| Example 4 | 60 | 37 | 63 |
| Example 5 | 60 | 35 | 53 |
| Example 6, (comparison) | 60 | 34 | 57 |
| Example 7, (comparison) | 60 | 31 | 51 |

FIGS. 2a and 2b illustrate the connection, given in the table of Example 8, between the degree of alkoxylation (alkylene oxide content) in moles of alkylene oxide per mole of alkoxylated compound (EO-[mol/mol]), plotted on the ordinate, and the washing result, expressed by the degree of reflectance in %, plotted on the abscissa.

FIG. 2a shows the washing result in the case of the use of the EMPA 101 test material, and FIG. 2b shows the washing result in the case of the use of the wfk 10 D test material. The reference numerals given in FIGS. 2a and 2b have the following meanings:

E40 washing with surfactants according to the invention at 40° C.,

E60 washing with surfactants according to the invention at 60° C.,

V40 washing with closest comparable known surfactants at 40° C.,

V60 washing with closest comparable known surfactants at 60° C.

EXAMPLE 15

Determination of the Oil Detachment

Small copper plates (2×6 cm) are supplied with 0.1 g of SN 200 mineral oil as accurately as possible. These plates are carefully dipped into a 0.1% strength surfactant solution from Examples 4–7 and Comparisons 9–13. The surfactant solution is not stirred. After 25 minutes, the plates are removed from the surfactant solution and dried in a drying cabinet at 70° C. for 5 hours, and the amount of oil is back-weighed. The results are summarized in Table 1 and shown graphically in FIG. 3.

TABLE

| Oil detachment on corner | |
|---|---|
| Surfactant according to | Amount of detached oil %, based on the startiun amount |
| Example 4 | 81 |
| Example 5 | 80.8 |
| Example 6 | 72.9 |
| Example 7 | 79.4 |
| Comparison 9 | 54.2 |
| Comparison 10 | 73.8 |
| Comparison 11 | 62.8 |
| Comparison 12 | 60.1 |
| Comparison 13 | 57.5 |

Figure 1:
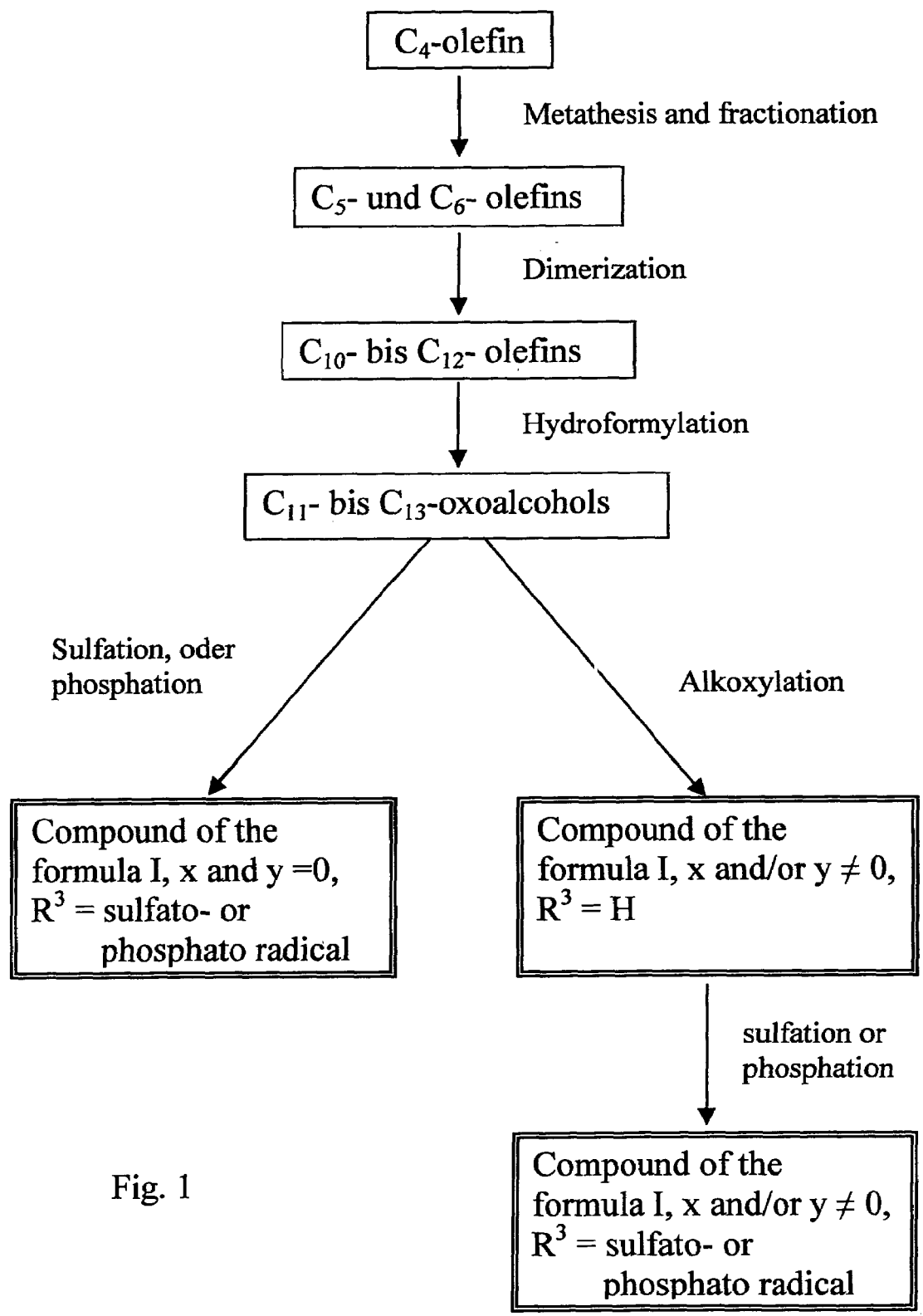
Figure 3:
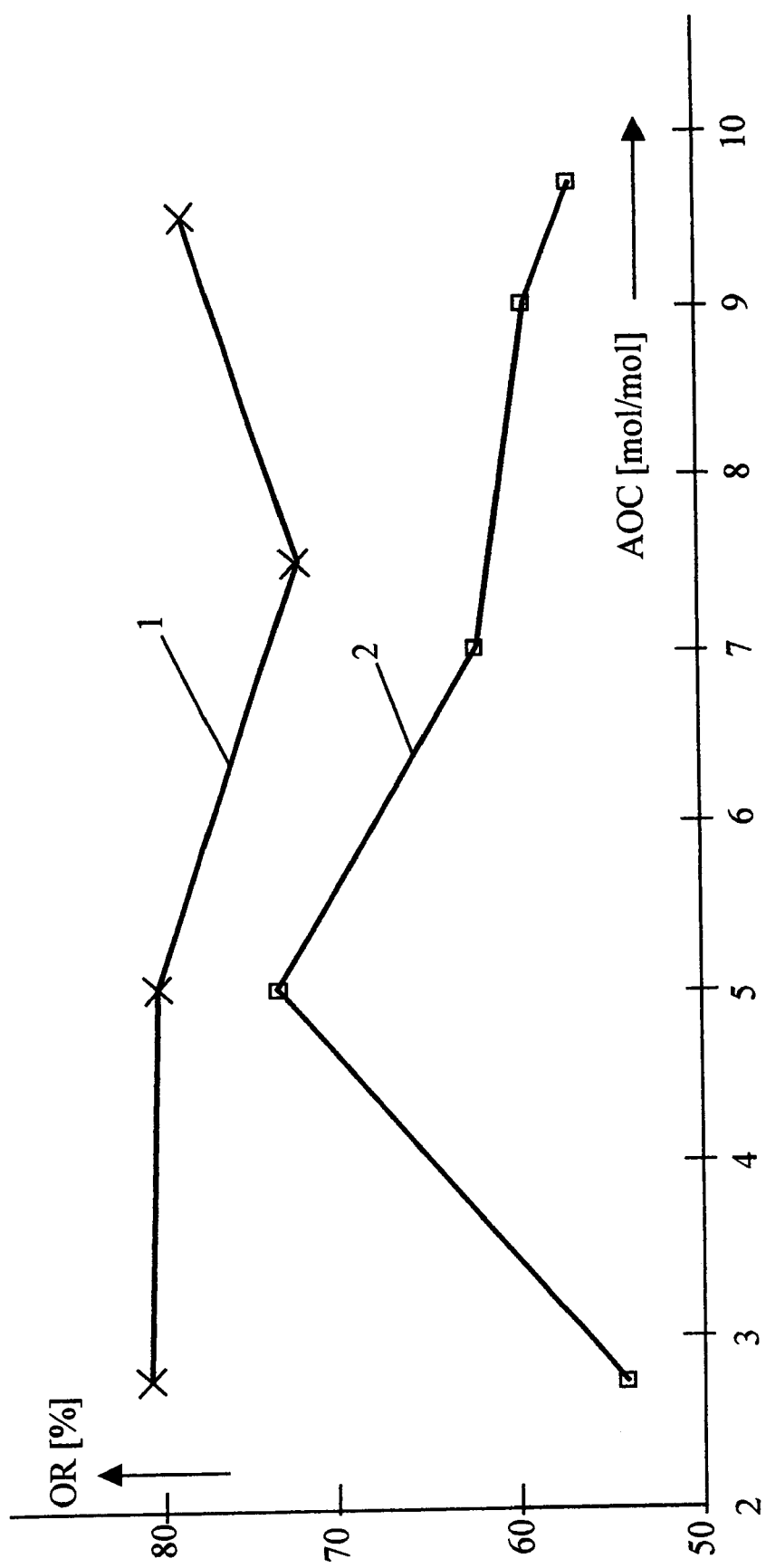

FIG. 3 illustrates the connection, given in the table above, between the degree of alkoxylation (alkylene oxide content) in moles of alkylene oxide per mole of alkoxylated compound, plotted on the ordinate, and the cleaning action, expressed by the oil detachment in % of the amount of oil applied, plotted on the abscissa.

EXAMPLE 16

Preparation of an Alkylphosphate 300 g of $C_{13}$-oxo alcohol (prepared by dimerization of 3-hexene and subsequent hydroformylation) are heated to 60° C. in a stirred vessel with nitrogen, and 125 g of polyphosphoric acid are slowly added. The temperature must not exceed 65° C. Toward the end of the addition the temperature is increased to 70° C., and the mixture is stirred at this temperature for 1 hour.

The surface tension at a concentration of 1 g/l is 35.1 mN/m, measured in accordance with DIN 53914.

EXAMPLE 17

Preparation of an Alkyl Ether Phosphate 560 g of the $C_{13}$-oxo alcohol ethoxylate prepared in Example 8 are heated to 60° C. in a stirred vessel under nitrogen, and 92 g of polyphosphoric acid are slowly added. The temperature must not exceed 65° C. Toward the end of the addition the temperature is increased to 70° C., and the mixture is stirred at this temperature for 1 hour.

The surface tension at a concentration of 1 g/l is 31.7 mN/m, measured in accordance with DIN 53914.

EXAMPLE 18

Preparation of an Alkylsulfate 300 g of $C_{13}$-oxo alcohol (prepared by dimerization of 3-hexene and subsequent hydroformylation) are admixed slowly and under nitrogen in a stirred vessel with 198 g of chlorosulfuric acid. The temperature must not exceed 30° C. This mixture is added to a solution of 68 g of NaOH in 1060 ml of water.

The surface tension at a concentration of 1 g/l is 36.1 mN/m, measured in accordance with DIN 53914.

EXAMPLE 19

Preparation of an Alyl Ether Sulfate 420 g of the $C_{13}$-oxo alcohol ethoxylate prepared in Example 8 are heated to 60° C. in a stirred vessel under nitrogen, and 198 g of chlorosulfuric acid are slowly added. The temperature must not exceed 30° C. This mixture is added to a solution of 68 g of NaOH in 1500 ml of water.

The surface tension at a concentration of 1 g/l is 33.1 mN/m, measured in accordance with DIN 53914.

We claim:

1. Detergents and cleaners comprising an effective proportion of one or more surfactants of the formula I:

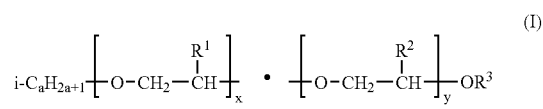

wherein:
 a is one of the numbers 11, 12, or 13,
 whereby the i-$C_aH_{2a+1}$ radical is derived from an oxo alcohol obtained by hydroformylation of a decene, dodecene or a mixture of these olefins which, in turn, has been prepared by dimerizing n-pent-2-ene, hex-3-ene or mixtures of these compounds;
 $R^1$ and $R^2$ are different and are each hydrogen or alkyl radicals of the formula $C_{H2n+1}$;
 $R^3$ is a hydrogen, or a sulfato or phosphato radical;
 n is a number from 1 to 16, x is a number from 0 to 200, and y is a number from 0 to 200;
wherein the surfactants of the formula I are prepared by:
 a) subjecting but-1-ene and but-2-ene to metathesis in the presence of molybdenum, tungsten or rhenium compounds as catalysts,
 b) separating off pent-2-ene and hex-3-ene from the metathesis mixture,
 c) subjecting the separated-off olefins individually or in a mixture to a dimerization to give olefin mixtures having 10 to 12 carbon atoms,
 d) subjecting the resulting olefin mixture, optionally after fractionation, to hydroformylation by reaction with carbon monoxide and hydrogen in the presence of a cobalt- or rhodium-containing catalyst to give a mixture of oxo alcohols,
 e) optionally alkoxylating the resulting oxo alcohols, and
 f) where appropriate, converting the oxo alcohols or oxo alcoholalkoxylates obtained in preparation step d) or e) into the acidic sulfuric or phosphoric esters;

and further comprising auxiliaries and additives for detergents and cleaners, and optionally additional surfactants, wherein at the branching sites of the main chain predominantly groups having (y−4) and (y−5) carbon atoms are bonded, where y is the number of carbon atoms in the monomer used for the dimerization, and the value (y−5)=0 means that no side chains are present, and the properties of monosubstitution products (single branching) in the olefin mixture are in total in the range from 40 to 75% by weight, and the proportions of double-branched components are in the range from 5 to 25% by weight.

2. The detergents as claimed in claim 1, wherein the proportion of the surfactants of the formula I in the detergent, based on the total weight of the composition, is 0.01 to 50% by weight.

3. The cleaners as claimed in claim 1, wherein the proportion of the surfactants of the formula I in the cleaners, based on the total weight of the composition, is 0.01 to 40% by weight.

4. The detergents and cleaners as claimed in claim 1, wherein, in the surfactants of the formula I, a is 13.

5. The detergents and cleaners as claimed in claim 1, wherein, in the surfactants of the formula I, $R^1$ and $R^2$ are different and are each hydrogen, methyl, ethyl, or propyl.

6. A process for the preparation of detergents and cleaners, comprising adding the surfactants of the formula I as defined in claim 1 to the detergents and cleaners.

7. A washing process comprising applying the detergents of claim 1 to more or less flexible materials comprising natural, synthetic or semisynthetic fiber materials and which at least partially have a textile character.

8. A process for the cleaning of continuous surfaces, comprising applying the cleaners of claim 1 to the continuous surfaces.

9. The detergents as claimed in claim 2, wherein the proportion of the surfactants of the formula I in the detergent, based on the total weight of the composition, is 0.1 to 40% by weight.

10. The cleaners as claimed in claim 3, wherein the proportion of the surfactants of the formula I in the cleaners, based on the total weight of the composition, is 0.1 to 30% by weight.

11. A process as claimed in claim 8, wherein the continuous surfaces are hard surfaces.

* * * * *